United States Patent
Green

(10) Patent No.: US 7,701,209 B1
(45) Date of Patent: Apr. 20, 2010

(54) COILS FOR HORIZONTAL FIELD MAGNETIC RESONANCE IMAGING

(75) Inventor: Charles A. Green, Holbrook, NY (US)

(73) Assignee: Fonar Corporation, Melville, NY (US)

(*) Notice: Subject to any disclaimer, the term of this patent is extended or adjusted under 35 U.S.C. 154(b) by 493 days.

(21) Appl. No.: 10/998,395

(22) Filed: Nov. 29, 2004

Related U.S. Application Data

(63) Continuation-in-part of application No. 10/266,070, filed on Oct. 7, 2002, now abandoned.

(60) Provisional application No. 60/327,329, filed on Oct. 5, 2001, provisional application No. 60/342,832, filed on Dec. 20, 2001.

(51) Int. Cl.
G01V 3/00 (2006.01)
(52) U.S. Cl. .................. 324/307; 324/318
(58) Field of Classification Search ......... 324/300–322; 600/410–435
See application file for complete search history.

(56) References Cited

U.S. PATENT DOCUMENTS

| | | | |
|---|---|---|---|
| 3,810,254 A | 5/1974 | Utsumi et al. |
| 4,407,292 A | 10/1983 | Edrich et al. |
| 4,411,270 A | 10/1983 | Damadian |
| 4,534,076 A | 8/1985 | Barge |
| 4,534,358 A | 8/1985 | Young |
| D283,858 S | 5/1986 | Opsvik et al. |
| 4,608,991 A | 9/1986 | Rollwitz |
| 4,613,820 A | 9/1986 | Edelstein et al. |
| 4,614,378 A | 9/1986 | Picou |
| 4,629,989 A | 12/1986 | Riehl et al. |
| 4,641,119 A | 2/1987 | Moore |
| 4,651,099 A | 3/1987 | Vinegar et al. |
| 4,663,592 A | 5/1987 | Yamaguchi et al. |
| 4,664,275 A | 5/1987 | Kasai et al. |
| 4,668,915 A | 5/1987 | Daubin et al. |
| 4,672,346 A | 6/1987 | Miyamoto et al. |
| 4,675,609 A | 6/1987 | Danby et al. |
| 4,679,022 A | 7/1987 | Miyamoto et al. |
| 4,707,663 A | 11/1987 | Minkoff et al. |
| 4,766,378 A | 8/1988 | Danby et al. |
| 4,767,160 A | 8/1988 | Mengshoel et al. |

(Continued)

FOREIGN PATENT DOCUMENTS

DE 3140225 A1 4/1983

(Continued)

OTHER PUBLICATIONS

Feng, et al., A New Phased Array Spine Coil for Vertical Field MRI System, Proc. Intl. Soc. Mag. Reson. Med. 11, 2003.

(Continued)

*Primary Examiner*—Brij B Shrivastav
*Assistant Examiner*—Dixomara Vargas
(74) *Attorney, Agent, or Firm*—Lerner, David, Littenberg, Krumholz & Mentlik, LLP

(57) ABSTRACT

Apparatus for performing magnetic resonance imaging are disclosed. In one aspect coil antennas for use with a horizontal field magnetic resonance imaging apparatus are placed in proximity to the scanning region to obtain magnetic resonance images. The coils are arranged in quadrature geometry and housed in a planar structure.

8 Claims, 14 Drawing Sheets

U.S. PATENT DOCUMENTS

| | | | |
|---|---|---|---|
| 4,770,182 A | 9/1988 | Damadian et al. | |
| 4,777,464 A | 10/1988 | Takabatashi et al. | |
| 4,816,765 A | 3/1989 | Boskamp | |
| 4,829,252 A | 5/1989 | Kaufman | |
| 4,866,387 A | 9/1989 | Hyde et al. | |
| 4,875,485 A | 10/1989 | Matsutani | |
| 4,908,844 A | 3/1990 | Hasegawa | |
| 4,918,388 A * | 4/1990 | Mehdizadeh et al. | 324/322 |
| 4,920,318 A | 4/1990 | Misic et al. | |
| 4,924,198 A | 5/1990 | Laskaris | |
| 4,943,774 A | 7/1990 | Breneman et al. | |
| 4,968,937 A | 11/1990 | Akgun | |
| 4,985,678 A | 1/1991 | Gangarosa et al. | |
| 5,008,624 A | 4/1991 | Yoshida | |
| 5,030,915 A | 7/1991 | Boskamp et al. | |
| 5,050,605 A | 9/1991 | Eydelman et al. | |
| 5,061,897 A | 10/1991 | Danby et al. | |
| 5,062,415 A | 11/1991 | Weatherby et al. | |
| 5,065,701 A | 11/1991 | Punt | |
| 5,065,761 A | 11/1991 | Pell | |
| 5,081,665 A | 1/1992 | Kostich | |
| 5,124,651 A | 6/1992 | Danby et al. | |
| 5,134,374 A | 7/1992 | Breneman et al. | |
| 5,153,517 A * | 10/1992 | Oppelt et al. | 324/322 |
| 5,153,546 A | 10/1992 | Laskaris | |
| 5,155,758 A | 10/1992 | Vogl | |
| 5,162,768 A | 11/1992 | McDougall et al. | |
| 5,171,296 A | 12/1992 | Herman | |
| 5,194,810 A | 3/1993 | Breneman et al. | |
| 5,197,474 A | 3/1993 | Englund et al. | |
| 5,207,224 A | 5/1993 | Dickinson et al. | |
| 5,221,165 A | 6/1993 | Goszczynski | |
| 5,221,902 A | 6/1993 | Jones et al. | |
| 5,229,723 A | 7/1993 | Sakurai et al. | |
| 5,250,901 A | 10/1993 | Kaufman et al. | |
| 5,251,961 A | 10/1993 | Pass | |
| 5,256,971 A | 10/1993 | Boskamp | |
| 5,274,332 A | 12/1993 | Jaskolski | |
| 5,291,890 A | 3/1994 | Cline et al. | |
| 5,304,932 A | 4/1994 | Carlson | |
| 5,305,365 A | 4/1994 | Coe | |
| 5,305,749 A | 4/1994 | Li et al. | |
| 5,315,244 A | 5/1994 | Griebeler | |
| 5,315,276 A | 5/1994 | Huson et al. | |
| 5,317,297 A | 5/1994 | Kaufman et al. | |
| 5,323,113 A * | 6/1994 | Cory et al. | 324/318 |
| 5,349,956 A | 9/1994 | Bonutti | |
| 5,382,904 A | 1/1995 | Pissanetzky | |
| 5,382,905 A | 1/1995 | Miyata et al. | |
| 5,386,447 A | 1/1995 | Siczek | |
| 5,394,087 A | 2/1995 | Molyneaux | |
| 5,412,363 A | 5/1995 | Breneman et al. | |
| 5,436,607 A | 7/1995 | Chari et al. | |
| 5,471,142 A | 11/1995 | Wang | |
| 5,473,251 A | 12/1995 | Mori | |
| 5,475,885 A | 12/1995 | Ishikawa | |
| 5,477,146 A | 12/1995 | Jones | |
| 5,490,513 A | 2/1996 | Damadian et al. | |
| 5,515,863 A | 5/1996 | Damadian | |
| 5,519,372 A | 5/1996 | Palkovich et al. | |
| 5,548,218 A * | 8/1996 | Lu | 324/318 |
| 5,553,777 A | 9/1996 | Lampe | |
| 5,566,681 A | 10/1996 | Manwaring et al. | |
| 5,578,925 A | 11/1996 | Molyneaux et al. | |
| 5,592,090 A | 1/1997 | Pissanetzky | |
| 5,606,970 A | 3/1997 | Damadian | |
| 5,621,323 A * | 4/1997 | Larsen | 324/318 |
| 5,623,241 A | 4/1997 | Minkoff | |
| 5,640,958 A | 6/1997 | Bonutti | |
| 5,652,517 A | 7/1997 | Maki et al. | |
| 5,654,603 A | 8/1997 | Sung et al. | |
| 5,666,056 A | 9/1997 | Cuppen et al. | |
| 5,671,526 A | 9/1997 | Merlano et al. | |
| 5,680,861 A | 10/1997 | Rohling | |
| 5,682,098 A * | 10/1997 | Vij | 324/318 |
| 5,735,278 A | 4/1998 | Hoult et al. | |
| 5,743,264 A | 4/1998 | Bonutti | |
| 5,754,085 A | 5/1998 | Danby et al. | |
| 5,779,637 A | 7/1998 | Palkovich et al. | |
| 5,836,878 A | 11/1998 | Mock et al. | |
| 5,862,579 A | 1/1999 | Blumberg et al. | |
| 5,929,639 A * | 7/1999 | Doty | 324/318 |
| 5,951,474 A * | 9/1999 | Matsunaga et al. | 600/422 |
| D417,085 S | 11/1999 | Kanwetz, II | |
| 5,983,424 A | 11/1999 | Naslund | |
| 5,988,173 A | 11/1999 | Scruggs | |
| 6,008,649 A | 12/1999 | Boskamp et al. | |
| 6,011,396 A | 1/2000 | Eckels et al. | |
| 6,014,070 A | 1/2000 | Danby et al. | |
| 6,023,165 A * | 2/2000 | Damadian et al. | 324/318 |
| 6,075,364 A | 6/2000 | Damadian et al. | |
| 6,122,541 A | 9/2000 | Cosman et al. | |
| 6,137,291 A * | 10/2000 | Szumowski et al. | 324/318 |
| 6,138,302 A | 10/2000 | Sashin et al. | |
| 6,141,579 A | 10/2000 | Bonutti | |
| 6,144,204 A | 11/2000 | Sementchenko et al. | |
| 6,150,819 A | 11/2000 | Laskaris et al. | |
| 6,150,820 A | 11/2000 | Damadian et al. | |
| 6,201,394 B1 | 3/2001 | Danby et al. | |
| 6,208,144 B1 | 3/2001 | McGinley et al. | |
| 6,226,856 B1 | 5/2001 | Kazama et al. | |
| 6,246,239 B1 * | 6/2001 | Krogmann et al. | 324/318 |
| 6,246,900 B1 | 6/2001 | Cosman et al. | |
| 6,249,121 B1 * | 6/2001 | Boskamp et al. | 324/318 |
| 6,249,695 B1 * | 6/2001 | Damadian | 600/427 |
| 6,285,188 B1 | 9/2001 | Sakakura et al. | |
| 6,346,814 B1 | 2/2002 | Carrozzi et al. | |
| 6,357,066 B1 | 3/2002 | Pierce | |
| 6,369,571 B1 | 4/2002 | Damadian et al. | |
| 6,377,044 B1 * | 4/2002 | Burl et al. | 324/307 |
| 6,385,481 B2 | 5/2002 | Nose et al. | |
| 6,411,088 B1 | 6/2002 | Kuth et al. | |
| 6,414,490 B1 | 7/2002 | Damadian et al. | |
| 6,424,854 B2 | 7/2002 | Hayashi et al. | |
| 6,456,075 B1 | 9/2002 | Damadian et al. | |
| 6,504,371 B1 | 1/2003 | Damadian et al. | |
| 6,549,800 B1 | 4/2003 | Atalar et al. | |
| 6,591,128 B1 * | 7/2003 | Wu et al. | 600/422 |
| 6,639,406 B1 * | 10/2003 | Boskamp et al. | 324/318 |
| 6,677,753 B1 * | 1/2004 | Danby et al. | 324/318 |
| 6,792,257 B2 | 9/2004 | Rabe et al. | |
| 6,801,038 B2 | 10/2004 | Carrozzi et al. | |
| 6,806,711 B2 * | 10/2004 | Reykowski | 324/318 |
| 6,850,064 B1 | 2/2005 | Srinivasan | |
| 6,882,149 B2 | 4/2005 | Nitz et al. | |
| 6,882,877 B2 | 4/2005 | Bonutti | |
| 6,894,495 B2 | 5/2005 | Kan | |
| 6,954,069 B2 * | 10/2005 | Harvey et al. | 324/318 |
| 6,980,002 B1 * | 12/2005 | Petropoulos et al. | 324/318 |
| 7,046,006 B2 * | 5/2006 | Creemers | 324/318 |
| 7,049,819 B2 * | 5/2006 | Chan et al. | 324/319 |
| 7,221,161 B2 * | 5/2007 | Fujita et al. | 324/318 |
| 7,245,127 B2 * | 7/2007 | Feng et al. | 324/318 |
| 7,348,778 B2 * | 3/2008 | Chu et al. | 324/318 |
| 7,474,098 B2 * | 1/2009 | King | 324/318 |
| 2001/0029330 A1 | 10/2001 | Nose et al. | |
| 2002/0013524 A1 | 1/2002 | Hayashi et al. | |
| 2002/0032927 A1 | 3/2002 | Dinkler | |
| 2002/0101241 A1 | 8/2002 | Chui | |
| 2002/0123681 A1 | 9/2002 | Zuk et al. | |
| 2002/0196021 A1 | 12/2002 | Wang | |

| | | |
|---|---|---|
| 2003/0210049 A1 | 11/2003 | Boskamp et al. |

FOREIGN PATENT DOCUMENTS

| | | |
|---|---|---|
| JP | 1242056 | 9/1989 |
| JP | 4-332531 | 11/1992 |
| JP | 62-26052 | 8/1994 |
| JP | 08-050843 A | 2/1996 |
| WO | WO-97/17896 | 5/1997 |

OTHER PUBLICATIONS

Guclu et al., A method for Preamplifier-Decoupling Improvement in Quadrature Phased-Array Coils, Journal of Magnetic Resonance Imaging, 19:255-258, 2004.

U.S. Appl. No. 08/978,084, filed Nov. 25, 1997.

U.S. Appl. No. 10/131,843, filed Apr. 25, 2002.

U.S. Appl. No. 09/718,946, filed Nov. 22, 2000.

Weis et al., Simulation of the influence of magnetic field inhomogeneity and distortion correction in MR imaging, vol. 8, No. 4, p. 483-489, 1990 (Abstract).

"The design and construction of high field-uniformity permanent magnet system for MRI" Feng, Z.X.; Jiang, X.H.;Han, S.; Magnetics, IEEE Transactions on vol. 28, Issue 1, Jan. 1992 pp. 641-643.

* cited by examiner

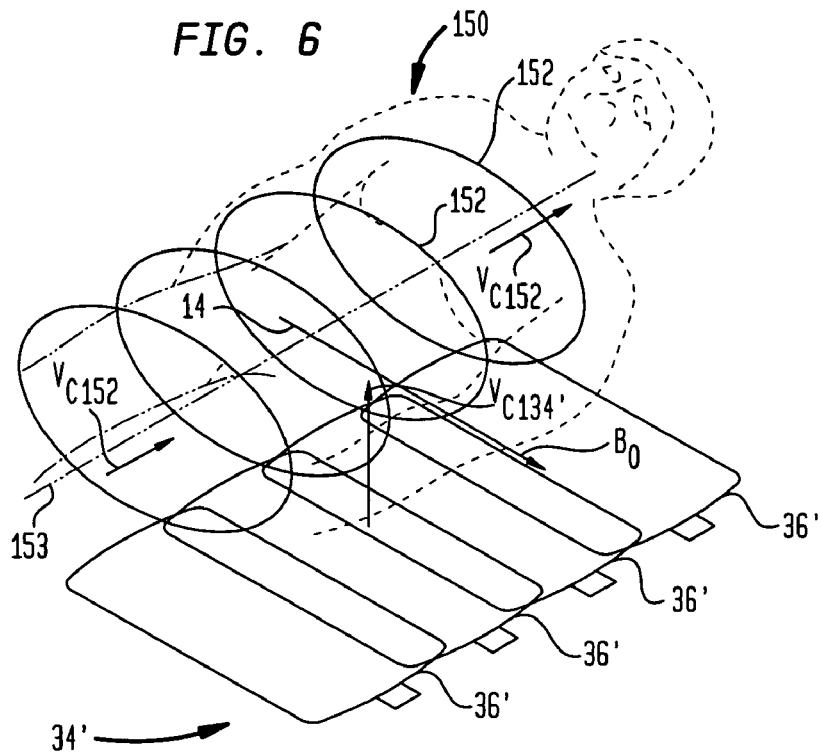
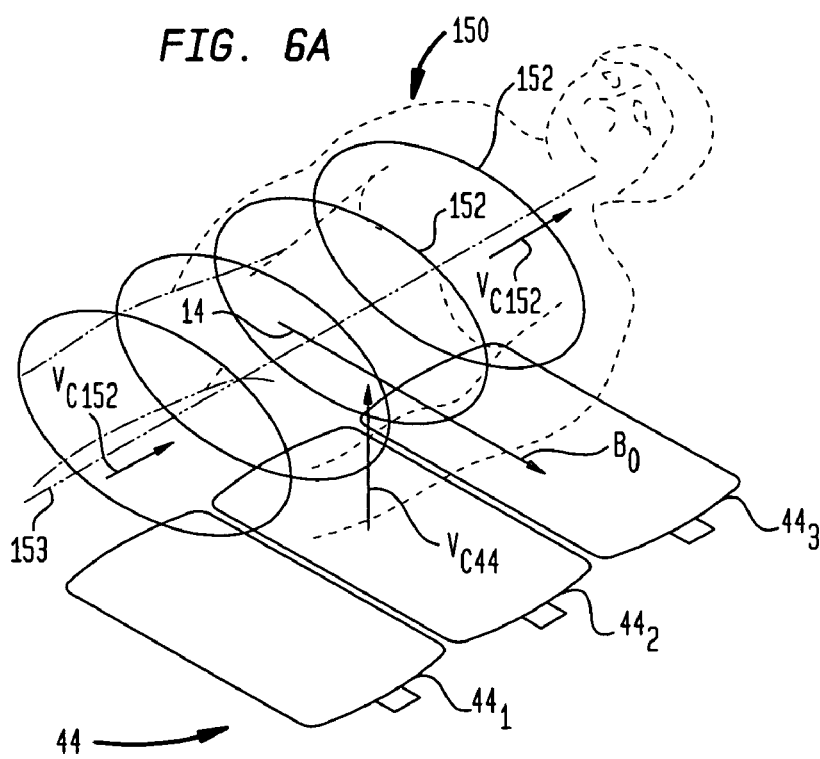

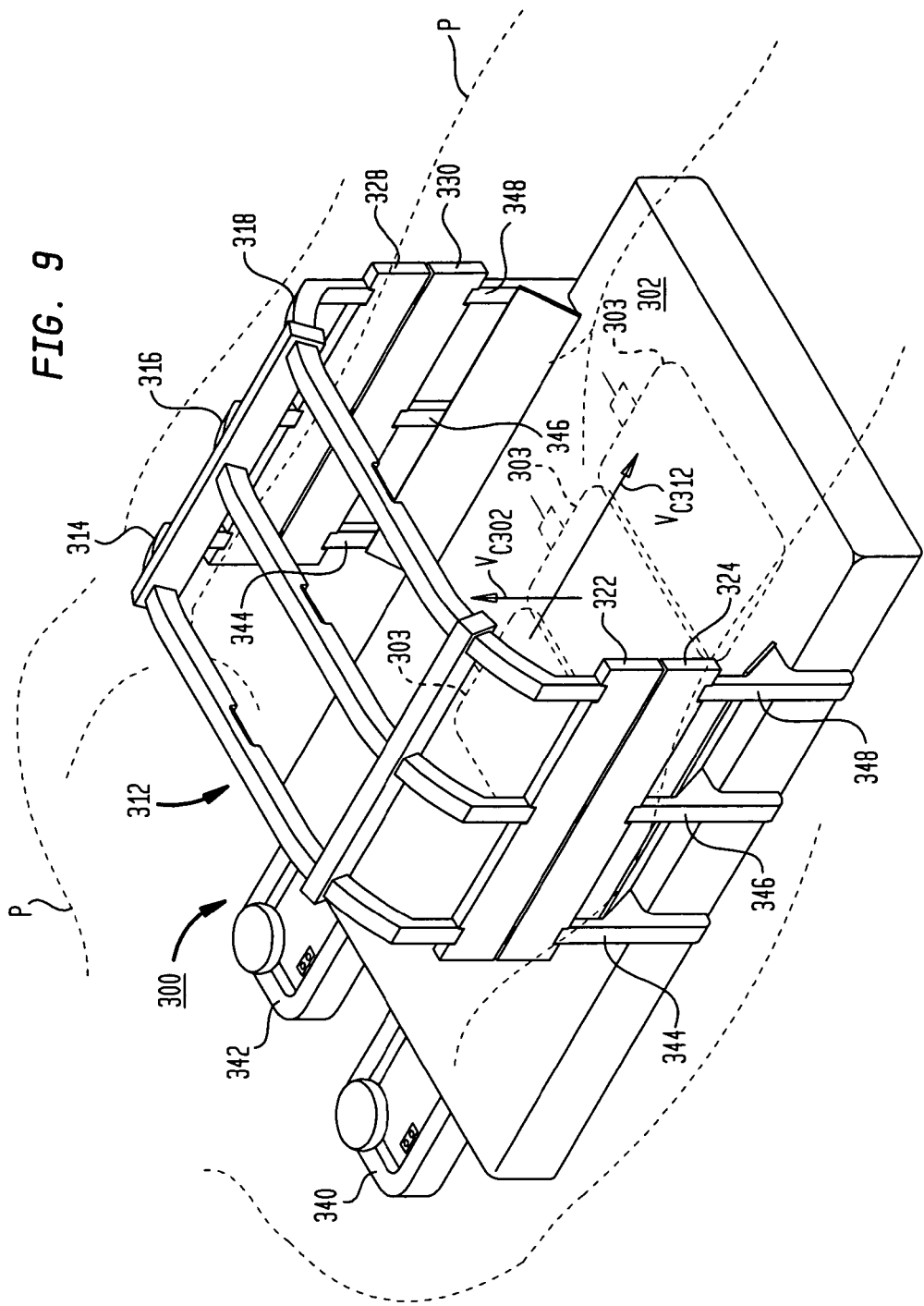

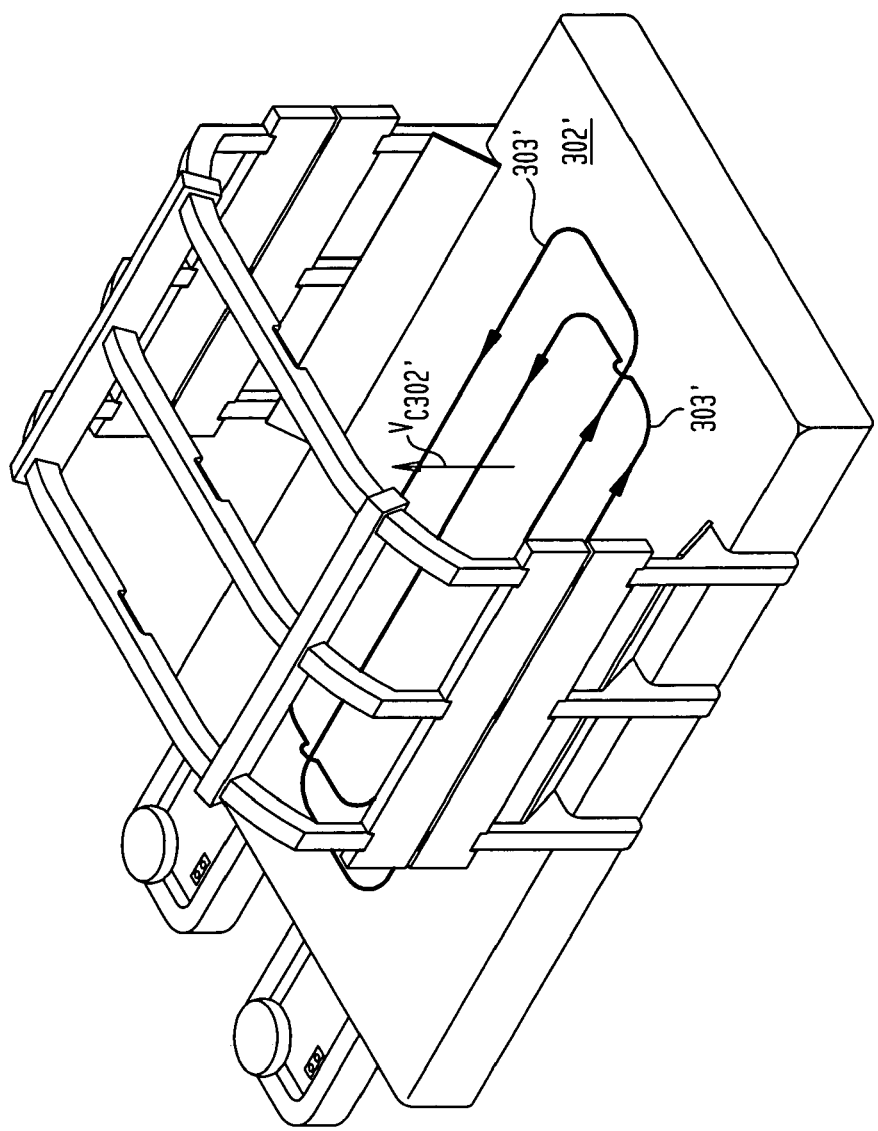

COILS FOR HORIZONTAL FIELD MAGNETIC RESONANCE IMAGING

CROSS REFERENCE TO RELATED APPLICATIONS

The present application is a continuation-in-part of U.S. application Ser. No. 10/266,070, filed Oct. 7, 2002, entitled "Coils For Horizontal Field Magnetic Resonance Imaging" and claims the benefit of the filing date of U.S. Provisional Application Nos. 60/327,329, filed Oct. 5, 2001 and 60/342,832, filed Dec. 20, 2001, the disclosures of which are hereby incorporated herein by reference.

BACKGROUND

The present invention relates to magnetic resonance imaging apparatus and procedures. In magnetic resonance imaging, an object to be imaged as, for example, a body of a human subject, is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals during the relaxation process, referred to herein as magnetic resonance signals. Different tissues produce different signal characteristics. Furthermore, relaxation times are a major factor in determining signal strength. In addition, tissues having a high density of certain nuclei will produce stronger signals than tissues with F a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. patent application Ser. No. 08/978,084, filed on Nov. 25, 1997, and U.S. Pat. Nos. 6,414,490 and 6,677,753, the disclosures of which are incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the aforesaid applications, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

Another physical constraint on MRI imaging has been posed by the requirements for RF antennas to transmit the RF excitation energy and to receive the magnetic resonance signals from the patient. The antenna that receives the signals is positioned near that portion of the patient's body that is to be imaged so as to maximize the signal-to-noise ratio and improve reception of the weak magnetic resonance signals. The antenna that applies RF excitation energy can be positioned in a similar location to maximize efficiency of the applied RF energy. In some cases, the same antenna is used to apply RF excitation energy and to receive the magnetic resonance signals at different times during the process. However, it is often desirable to provide two separate antennas for this purpose.

The antennas are typically formed as one or more loops of electrically conductive material. Such a loop antenna must be positioned so that the conductor constituting the loop extends along an imaginary plane or surface having a normal vector transverse to the direction of the static magnetic field. Stated another way, the antenna must be arranged to transmit or receive electromagnetic fields in a direction perpendicular to the direction of the static magnetic field if it is to interact with the precessing atomic nuclei. This requirement has further limited available antenna configurations and techniques. For example, in a vertical-field magnet such as a ferromagnetic frame magnet having a vertical pole axis, it is impossible to use a loop antenna with the loop disposed generally in a horizontal plane below the body of a recumbent patient. Such an antenna has a normal vector which is vertical and hence parallel to the direction of the static magnetic field. A loop antenna which encircles the patient with its normal vector extending horizontally can be employed. Also, planar or saddle-shaped loops extending in generally vertical planes or surfaces, and having normal vectors in the horizontal direction transverse to the long axis of the patient can be positioned on opposite sides of the patient. However, these antenna configurations do not provide optimum signal-to-noise ratios in some procedures as, for example, in imaging the spine, head or pelvic region.

SUMMARY OF THE INVENTION

In accordance with an embodiment of the present invention an apparatus for magnetic resonance imaging comprises a magnet having a patient-receiving space and a horizontal pole axis. The magnet desirably includes a source of magnetic flux that provides a static magnetic field with a field vector in a substantially horizontal direction. A patient-positioning and antenna assembly is used in combination with the magnet to position and image the region of the patient's anatomy which is of interest within the patient-receiving space. The patient-positioning and antenna assembly desirably includes a patient support having a support surface adapted to support a surface of a human body. The antenna assembly preferably includes a first antenna including one or more coils, at least some of the coils extending along coil surfaces substantially parallel to the support surface and adjacent thereto, whereby a surface of a body supported by the support surface will closely overlie the coils. The patient-positioning and antenna assembly further includes a frame for holding the patient support so that a vector normal to the support surface and the coil surface extends transverse to the pole axis and transverse to said field vector. In accordance with this embodiment of the present invention, the coils are positioned in close proximity to the region of the patient's anatomy to be imaged so that the image obtained provides more detailed information for analysis.

In accordance with another aspect of the present invention an apparatus for magnetic resonance imaging preferably comprises a magnet defining a patient-receiving space and having a static magnetic field with a field vector in a substantially horizontal direction. The apparatus desirably includes a quadrature coil antenna arrangement for receiving a signal from an object or patient disposed within the patient receiving space. The quadrature coil antenna includes a first antenna having a first coil vector and a second antenna having a second coil vector, the first and second coil vector being transverse to the static magnetic field vector. Further in accordance with this aspect of the present invention, the static magnetic field vector is oriented substantially transverse to the long axis of the patient disposed in the receiving space. This embodiment advantageously provides for better signal-to-noise performance during scanning through the use of the quadrature coil arrangement.

In yet another aspect in accordance with the present invention, an antenna arrangement for horizontal field magnetic resonance imaging preferably comprises a first antenna having a first coil vector and a second antenna having a second coil vector. The first and second antennas being desirably arranged so that the first coil vector and second coil vector are substantially transverse to each other. In addition, the first and second antennas are further desirably arranged so that the first coil vector and the second coil vector are substantially transverse to the horizontal magnetic field. In accordance with this aspect of the present invention, the static magnetic field vector is oriented substantially transverse to the long axis of the patient disposed in the receiving space. Images taken in accordance with this aspect of the present invention benefit from the improvement in signal-to-noise ratio which results in images having more detail for the operator, medical professional or user.

In another embodiment in accordance with the present invention, a magnetic resonance imaging apparatus preferably comprises a stationary magnet having a pair of elements spaced apart from one another along a horizontal axis and a patient-receiving space between the elements in combination with a quadrature coil antenna arrangement. The magnet is operable to direct magnetic flux between the elements through the patient receiving space. The antenna assembly preferably includes a first antenna having a first coil vector and a second antenna having a second coil vector. The first coil vector and second coil vector are oriented substantially transverse to the horizontal magnetic field and the horizontal magnetic field is oriented substantially transverse to the long axis of the patient disposed within the patient receiving space.

In accordance with a method aspect of the invention method for magnetic resonance imaging is provided. The method preferably comprises the steps of providing a static magnetic field in a space, the static magnetic field having a substantially horizontal magnetic field vector and positioning a patient on a patient support surface so that the patient's body preferably overlies the support and overlies one or more coils of a first antenna, the one or more coils having coil surfaces substantially parallel to the support surface and adjacent thereto. The patient support surface is then desirably positioned in the static field so that the vectors normal to the coil surfaces are substantially transverse to the field vector and magnetic resonance signals are elicited by transmitting RF energy to the body and receiving said magnetic resonance signals, at least one of the transmitting and receiving steps being performed at least in part by use of the first antenna.

In another aspect, the present invention is an apparatus for magnetic resonance imaging. The apparatus preferably comprises a magnet defining a patient-receiving space and having a static magnetic field with a field vector in a substantially horizontal direction and a patient support having a support surface for a human body. The patient support is preferably positioned within said patient-receiving space and is preferably pivotable about a horizontal pivot axis. The apparatus further desirably includes a quadrature coil antenna arrangement for receiving a signal from a patient disposed within the receiving space. The quadrature coil antenna preferably includes a first antenna having a first coil vector and a second antenna having a second coil vector, the first coil vector and said second coil vector being substantially transverse to said static magnetic field vector. The static magnetic field vector is preferably oriented substantially transverse to the long axis of a patient disposed within the patient-receiving space.

In accordance with this aspect of the present invention, the first antenna and the second antenna each comprise a coil antenna configured in a butterfly geometry.

Further in accordance with this aspect of the present invention, the first antenna and the second antenna are desirably housed in a planar structure. Further still, the planar structure comprises a quadrature surface coil that is circularly polarized in a plane perpendicular to said magnetic field axis. In addition, the first and second coil vectors are preferably transverse to each other. It is further desirably if the planar structure can be adjusted along a lengthwise direction of the patient support surface perpendicular to the magnetic field axis.

In another aspect the present invention is a magnetic resonance imaging apparatus comprising a stationary magnet having a pair of elements spaced apart from one another along a horizontal axis and a patient-receiving space between the elements. The horizontal axis is preferably substantially transverse to the long axis of a patient disposed within the patient-receiving space on a bed pivotable about an horizontal axis and the magnet is preferably operable to direct flux between said elements through said patient-receiving space.

In accordance with this aspect of the present invention, the apparatus further desirably comprises a quadrature coil antenna arrangement for receiving a signal from a body disposed within the patient-receiving space, the quadrature coil antenna including a first antenna having a first coil vector and a second antenna having a second coil vector, the first coil vector and the second coil vector being oriented substantially transverse to each other. In addition, the quadrature coil antenna arrangement is preferably housed in a planar structure having a planar surface in a plane perpendicular to the magnetic field axis.

In another aspect the present invention comprises a system for magnetic resonance imaging comprising a magnet defining a patient-receiving space and having a static magnetic field with a field vector in a substantially horizontal direction; a patient support having a surface capable of supporting a human body, the patient support being positioned within the patient-receiving space and being pivotable about a horizontal pivot axis parallel to the static magnetic field vector; and a quadrature coil antenna arrangement for receiving magnetic resonance signals from a patient disposed within the receiving space adjacent the patient support surface, the quadrature coil antenna including a first antenna having a first coil vector and a second antenna having a second coil vector, the first coil vector and the second coil vector being transverse to the static magnetic field vector.

In accordance with this aspect of the present invention, the first antenna desirably comprises a loop coil antenna and the second antenna comprises a butterfly coil antenna. In addition, the planar structure preferably comprises a quadrature surface coil that is circularly polarized in a plane perpendicular to said magnetic field axis.

Further in accordance with this aspect of the present invention, the planar structure is preferably adjustable along a lengthwise direction of the bed's surface perpendicular to the magnetic field axis.

Further in accordance with this aspect of the present invention, the first antenna preferably comprises a coil antenna configured as loop coil and the second antenna preferably comprises an antenna configured as a butterfly coil.

In another aspect, the present invention is an apparatus for magnetic resonance imaging. The apparatus preferably comprises a magnet defining a patient-receiving space and having a static magnetic field with a field vector in a substantially horizontal direction; a patient support having a support surface for a human body, said patient support being positioned within said patient-receiving space and being pivotable about a horizontal pivot axis; and a quadrature coil antenna arrangement for receiving a signal from a patient disposed within said receiving space, said quadrature coil antenna including a first antenna having a first coil vector and a second antenna having a second coil vector, said first coil vector and said second coil vector being transverse to said static magnetic field vector, and wherein said static magnetic field vector is oriented substantially transverse to the long axis of a patient disposed within said patient-receiving space. In accordance with this aspect of the present invention, the first antenna comprises a loop coil antenna and the second antenna comprises a coil antenna configured in a butterfly geometry.

In accordance with this aspect of the present invention, the loop coil antenna magnetic sensitivity is aligned anterior to posterior with respect to an anatomy of a patient supported by the patient support. It may also be desirable if the butterfly coil antenna geometry is aligned inferior to posterior with respect to an anatomy of a patient supported by the patient support.

BRIEF DESCRIPTION OF THE DRAWINGS

FIG. 6 illustratively depicts a perspective view of first and second antennas in accordance with an aspect of the present invention;

FIG. 6A illustratively depicts a perspective view of first and second antennas in accordance with a further aspect of the present invention;

FIG. 9 illustrates an embodiment of a quadrature coil antenna having solenoidal coil antenna and a planar coil antenna;

FIG. 9A illustrates another embodiment of a quadrature coil antenna having solenoidal coil antenna and a planar coil antenna;

DETAILED DESCRIPTION OF THE PREFERRED EMBODIMENTS

Figure 1:
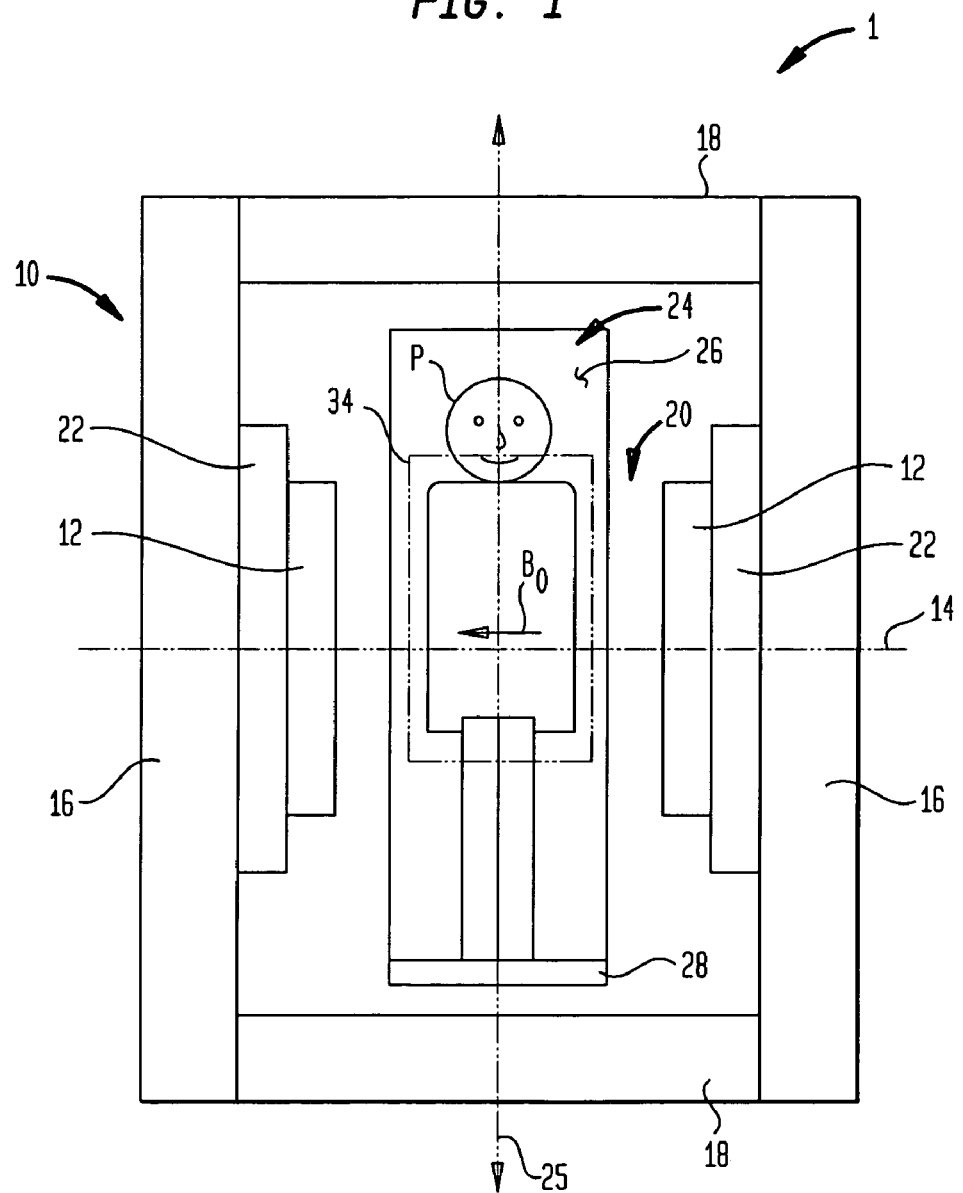
FIG. 1 illustratively depicts a front view of an apparatus in accordance with an embodiment of the present invention.
Figure 2:
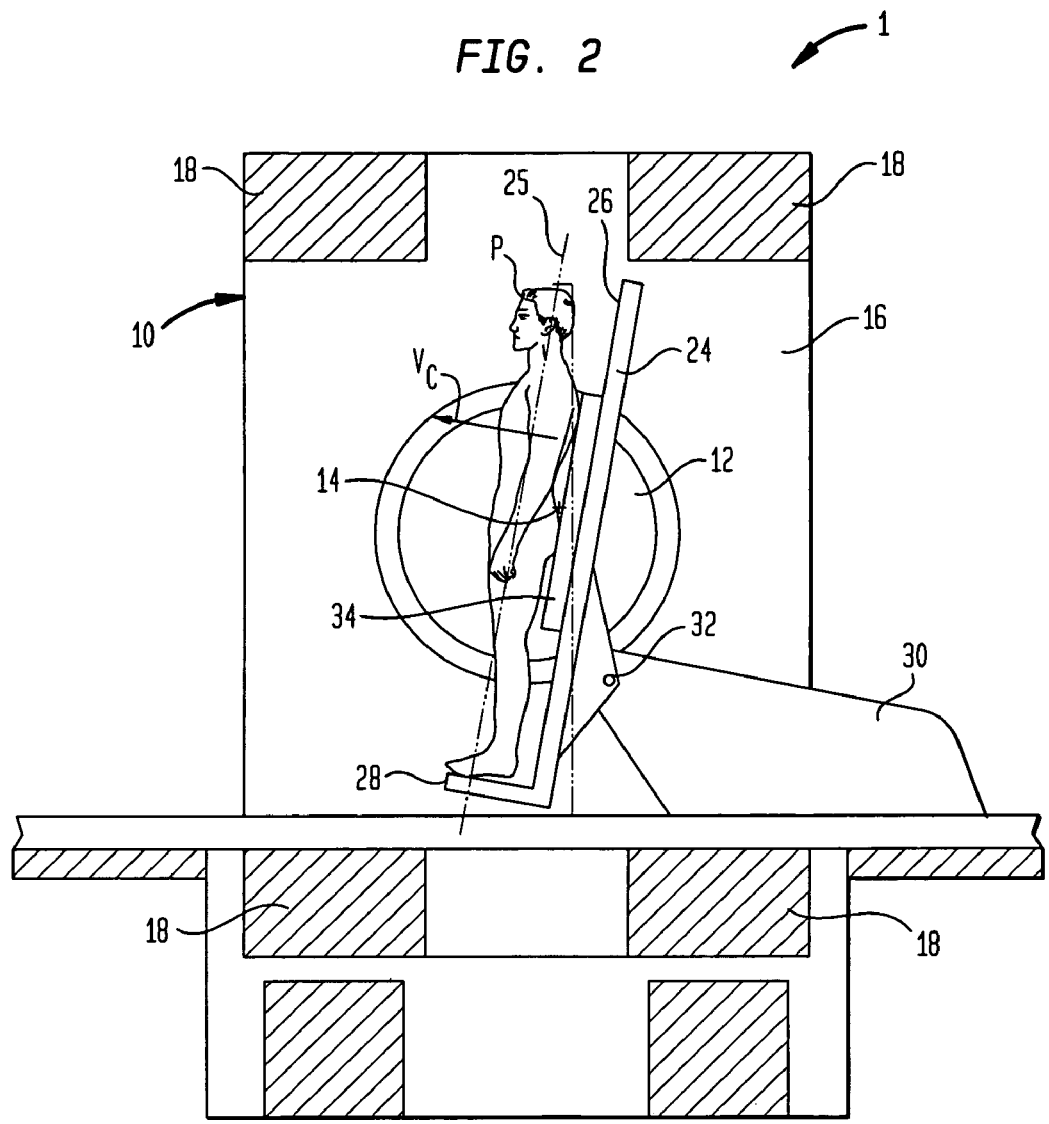
FIG. 2 is a side view of the apparatus of FIG. 1.

Turning to FIGS. 1 and 2, there is illustrated an apparatus 1 according to one embodiment of the present invention. The apparatus 1 includes a static field magnet having a frame 10 including a pair of poles 12 spaced apart from one another along a horizontal pole axis 14. Frame 10 further includes flux conducting and return members that, in the particular embodiment illustrated, include a pair of sidewalls 16 and columns 18 extending between the sidewalls 16. The particular frame depicted in FIGS. 1 and 2 is generally in accordance with the aforementioned U.S. Pat. No. 6,677,753, (hereinafter "the '753 patent") although other configurations can be employed. The opposed poles define a patient-receiving space or gap 20 between them. The magnet further includes a source of magnetic flux adapted to direct into and out of the gap through poles 12 so as to form a static magnetic field having a field vector $B_0$ in the horizontal direction, parallel to pole axis 14. In the particular embodiment illustrated, the flux source includes a pair of electromagnet coils 22 encircling poles 12. These coils may be superconductive or resistive coils. Alternate flux sources such as coils disposed at other locations along the ferromagnetic frame and permanent magnets also may be employed.

The apparatus further includes a patient support assembly including a bed 24 defining an elongated patient supporting surface 26 having a lengthwise axis 25 and a platform 28 projecting from the supporting surface at a foot end of the bed. In addition, a seat may be mounted to supporting surface 26 to allow a patient to be positioned in a sitting position. The patient supporting assembly further includes a frame 30. Bed 24 is pivotably mounted to the frame 30 for movement about a generally horizontal pivot axis 32. Pivot axis 32 is substantially parallel to pole axis 14. Bed 24 can pivot between an upright position in which the lengthwise direction over the bed extends generally vertically as seen in FIG. 2 and a fully horizontal position shown in FIG. 5, in which the lengthwise direction of the bed 24 extends horizontally. As further described in the '753 patent, bed 24 also may be mounted for vertical motion relative to frame 30 and hence relative to the static field magnet 10. Moreover, frame 30 can be mounted for horizontal movement relative to the static field magnet. Appropriate actuators and control devices (not shown) are provided for moving the bed and for moving support frame 30.

Figure 3:
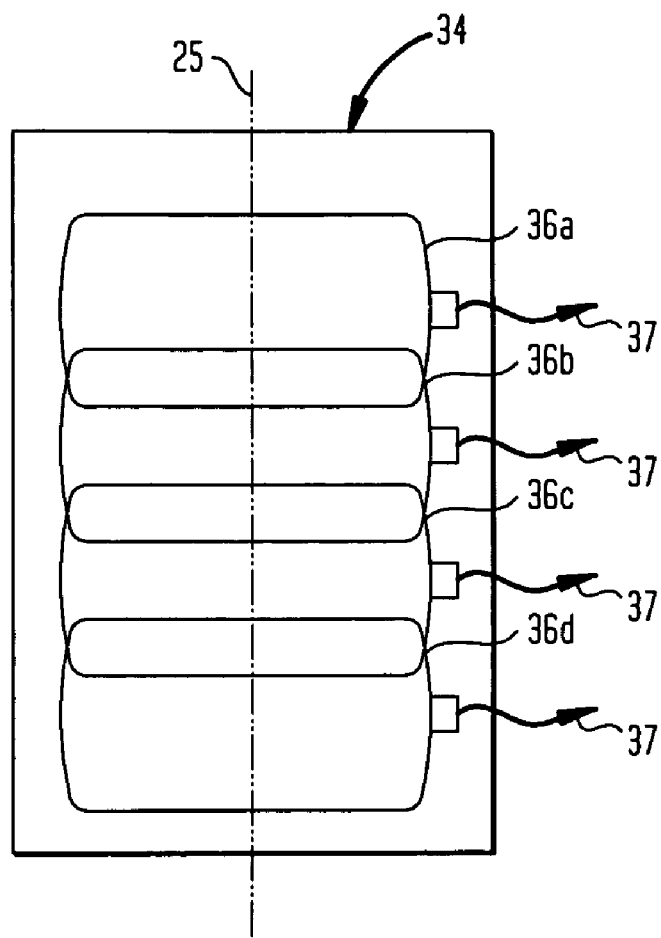
FIG. 3 illustratively depicts a top view of an antenna in accordance with an aspect of the present invention.
Figure 4:
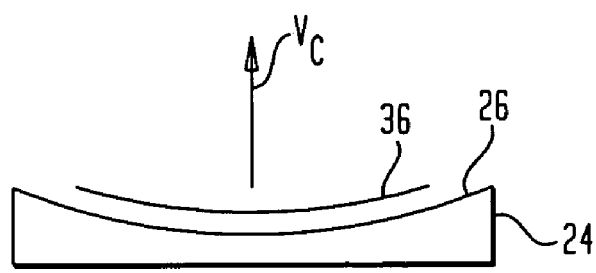
FIG. 4 is an edge view of the antenna of FIG. 3.
Figure 5:
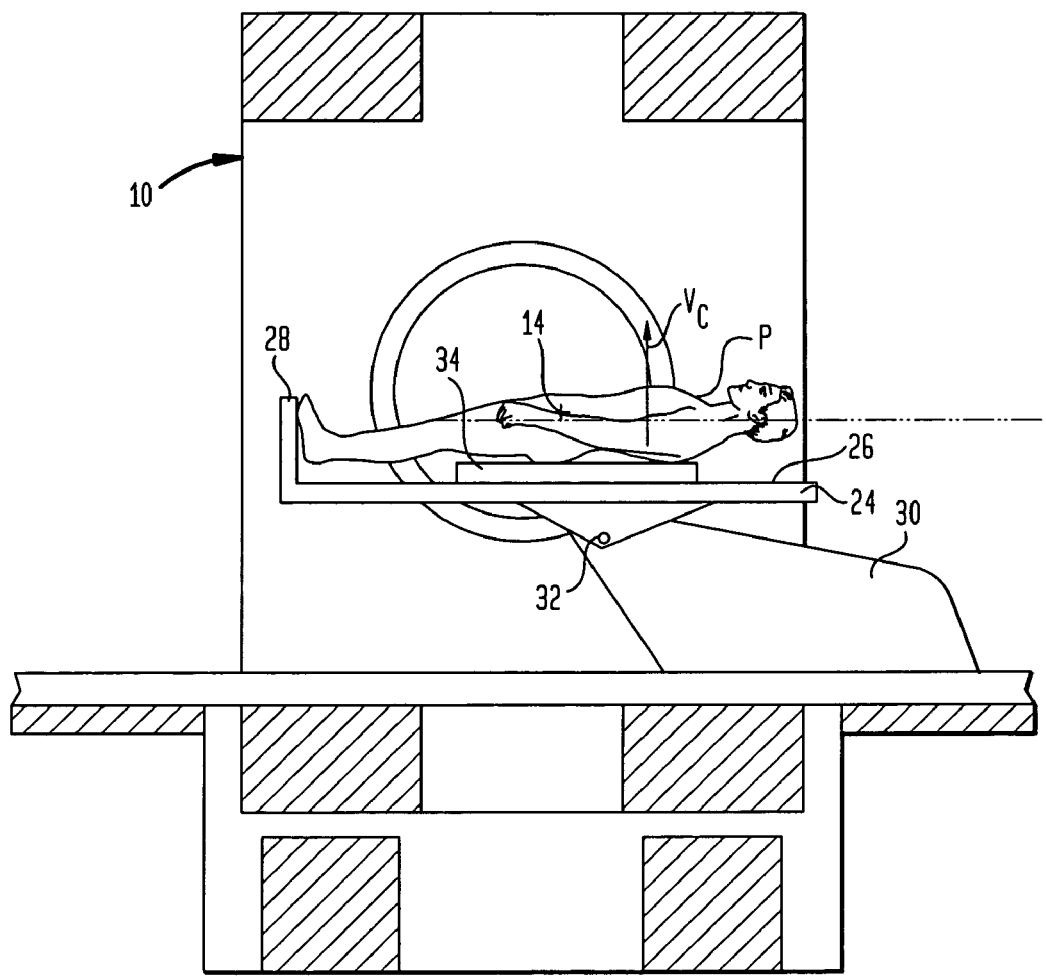
FIG. 5 is a side view of the apparatus of FIG. 1 with the patient depicted in a horizontal position.

The patient support assembly further includes a first antenna schematically depicted as a planar box 34 in FIGS. 1, 2 and 5. As best seen in FIGS. 3 and 4, the antenna includes a plurality of coils 36 each including a winding extending in a loop. Each loop may be provided with a conventional coupling to a separate coaxial cable or other output line 37 for conveying signals to a receiver or receiving signals from a transmitter. Also, each loop may include a capacitor (not shown) in series and/or in parallel with the conductor forming the loop so as to define a resonant antenna circuit. The windings of each coil extend along a slightly curved coil surface seen in edge view in FIG. 4. The term "coil surface" as used herein refers to an imaginary surface defined by the central axis of the conductors constituting the coil or antenna. For example, in the special case of a flat circular coil, the coil surface is the plane of the circle. Each coil surface defines a coil vector $V_c$ normal to the coil surface itself. In the case of a curved coil surface, the coil vector of the coil surface as a whole can be taken as the integral of the normal vector to the coil surface over the entire area of the coil surface inside the coil.

The coils 36 are arrayed along the lengthwise axis 25 of bed 24 so that the coils overlap one another as shown in FIG. 3. Such a mutual overlapping arrangement results in the coils having zero or nearly zero mutual inductance between the coils. Other arrangements which result in nearly zero mutual inductance include arranging the coils in a plane that may extend along an elongated patient support. Coil surfaces 36 extend generally parallel to the patient support surface 26 of bed 24. Thus, the normal vectors of the coil surfaces are transverse to the patient support surface 26 of the bed. The coils may be formed on a thin, plate or sheet that overlies surface 26. Alternatively, the coils 36 may be mounted inside of the bed so that the coils are disposed behind surface 26. Conventional padding or covering layers (not shown) may be provided over the coils and/or support surface 26 for patient comfort.

The apparatus also includes, or is used in conjunction with, conventional field gradient coils (not shown) for applying magnetic field gradients within the patient-receiving space or gap 20 and an RF receiver and transmitter (not shown) for applying RF signals through one or more loops 36 of antenna 34 and for receiving magnetic resonance signals using one or more loops 36. Additionally, the apparatus includes conventional control and reconstruction equipment for actuating the various elements discussed above including the gradient coils and RF transmitter and receiver to elicit magnetic resonance signals and to convert the resulting magnetic resonance signals into a set of data defining an image of the patient. These elements may use the conventional techniques and principles of the magnetic resonance art and accordingly are not discussed in detail herein.

In a method according to a further aspect of the invention, a patient P is disposed on patient support 24 so that the patient's body overlies the support and the first antenna 34. In the position illustrated, the posterior surface of the patient's torso is closely juxtaposed to the patient support and with the first antenna so that the patient's spine is adjacent to the first antenna. The anterior-posterior axis of the patient's body is parallel to the coil vector $V_c$ of the first antenna coils. The coil vector $V_c$ lies in a plane perpendicular to the pole axis 14. Thus, regardless of whether it is in an upright position as seen in FIG. 2 or in a fully horizontal position as seen in FIG. 5, or at any angle between these positions, the coil vector $V_c$ of the first antenna is perpendicular to the static magnetic field $B_0$ so that the coils of the first antenna can interact with the body tissue to excite the nuclei to receive magnetic resonance signals. This arrangement provides excellent signal-to-noise ratio. Any portion of the patient's spine can be imaged using any one or more of the coils 36A-36D in the first antenna. Further, this arrangement is entirely non-claustrophobic. The patient need not be constrained by the coils of the first antenna at all and the patient need not even be aware of the presence of the antenna.

Stated another way, the patient support surface 26 of support 24 lies substantially in a plane parallel to the pole axis 14 and hence parallel to the field vector of the static field magnet. This orientation allows the use of coils having coil surfaces generally parallel to the support surface. This arrangement of the support surface is different from the relative orientation of support surface and pole axis in a conventional "open" static field magnet having a vertical pole axis and a bed defining a substantially horizontal support surface, with the plane of the support surface perpendicular to the pole axis.

The same arrangement can be employed for imaging the patient in a prone position or standing position with the anterior surface of the torso facing the patient support surface 26. Also, this arrangement can be used with the patient in a sideways position, with his lateral axis (shoulder-to-shoulder axis), parallel to the coil vectors $V_c$. A similar arrangement can be used for imaging portions of the body other than the torso as, for example, the head or legs.

Turning now to FIG. 6, there is shown a perspective view of first and second antennas in accordance with another embodiment of the present invention. As FIG. 6 shows, a generally solenoidal second antenna 150 including a plurality of coils or loop windings 152 is used in conjunction with a first antenna 34 (similar to that discussed above). Each coil 152 of the second antenna extends in a plane transverse to the axis 153 of the antenna, and thus defines a coil having a coil vector $V_{c152}$ extending substantially parallel to the axis 153 of the solenoid and parallel to the coil vectors of the other coils. The solenoidal coils may be electrically coupled to one another using couplers (not shown) similar to those discussed above with reference to FIG. 3 or, preferably, may be electrically independent of one another. In any event, whether electrically coupled together or not, the solenoidal coils magnetically behave as one solenoidal coil, i.e., magnetic coupling is independent of electrical coupling. The first antenna 34' is similar to the first antenna 34 discussed above with reference to FIG.

3. The patient is positioned on the patient supporting surface (not shown) so that the patient overlies the first antenna 34 and so that the coils of the second antenna 150 encircle the patient's body. Solenoidal antennas that can be mounted so as to encircle the body of the patient in a convenient manner are disclosed, for example, in U.S. Pat. No. 4,887,038, the disclosure of which is hereby incorporated by reference herein. In FIG. 6, the patient and the second antenna 150 are depicted at a substantial distance above the first antenna 34' for clarity of illustration. In practice, the patient's body is positioned as close as is practicable to the first antenna.

In this arrangement, the coil vectors $V_{c152}$ of the second antenna are substantially perpendicular to the coil vectors $V_{c34'}$ of the first antenna and the coil vectors of both antennas are substantially perpendicular to the pole axis 14 and to the static field vector $B_0$, so that signals may be transmitted and/or received by either or both the first and second antennas. For example, the RF signals used to excite the nuclei may be transmitted by the second antenna and received by the first antenna or vice versa. Here again, the patient support may be arranged with the long axis of the patient's torso or other body structure horizontal or vertical.

Further in accordance with another aspect of the present invention, the first antenna 34' of FIG. 6 is replaced with a planar antenna of the type depicted in FIG. 6A. In particular, first antenna 44 includes one or more planar coil antennas, illustratively depicted as coils $44_1$ through $44_3$. Coils $44_1$ through $44_3$ each comprise one or more windings extending in a loop. Each coil, $44_1$ through $44_3$, includes a coil surface as described hereinabove. In addition, each coil surface defines a coil vector $V_{C44}$ normal to the coil surface. Although coils $44_1$ through $44_3$ do not overlap, as in the embodiment shown in FIGS. 3 and 4, the use of a planar antenna of the type depicted in FIG. 6A for first antenna 44 results in an improvement in the signal-to-noise ratio of up to $\sqrt{2}$.

Figure 7:
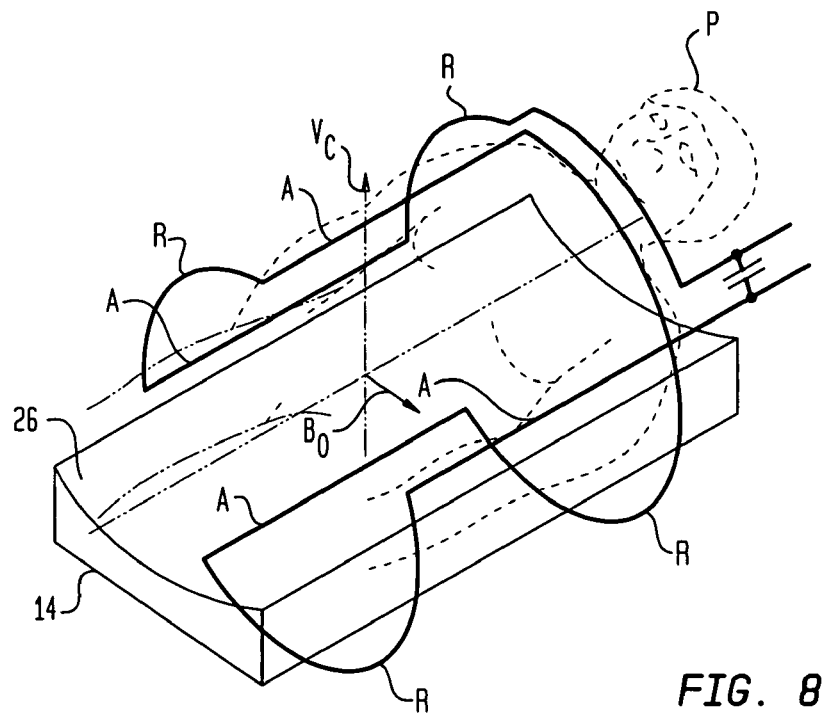
FIG. 7 schematically illustrates a saddle coil antenna in accordance with another aspect of the present invention.

In a further embodiment, schematically illustrated in FIG. 7, the first antenna is a saddle coil having a pair of windings each including a pair of axial runs A and a pair of arcuate runs R at the ends of the axial runs. Such a saddle coil defines a pair of coil surfaces in the form of sectors of a cylindrical surface. The coil vector of such a coil is perpendicular to the axis of the cylindrical surface. The first antenna may be arranged so that one of the saddle windings is disposed adjacent to the patient supporting surface 26 whereas the other is disposed remote from the patient supporting surface so that the patient's body is disposed between the two coils. Also, the first antenna may include additional sets of windings similar to the single set discussed above in reference to FIGS. 3 and 4. One set may be disposed adjacent the patient supporting surface whereas the other set may be disposed remote from the patient supporting surface, and the patient may be held between these two sets. A solenoidal coil similar to coil 150 discussed above can be used in conjunction with such a first antenna.

Figure 8:
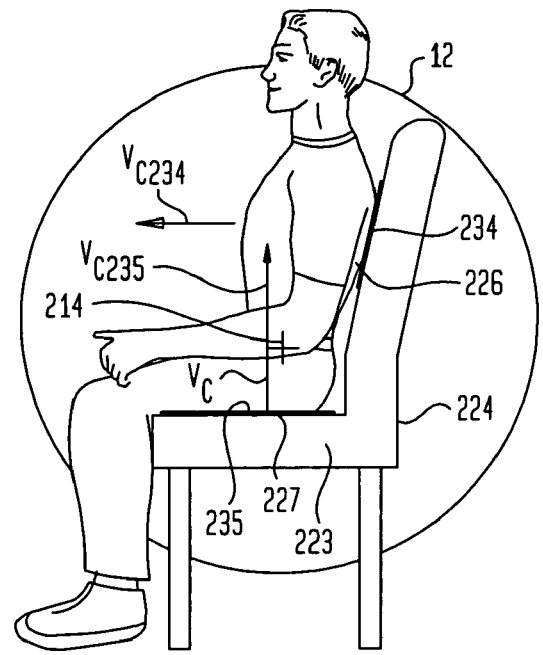
FIG. 8 illustratively depicts a patient support apparatus in accordance with another aspect of the present invention.

In a further variant, the patient support may have a K form other than an elongated bed. For example, as seen in FIG. 8, the patient support includes a chair having a seat 223 projecting in a forward or horizontal plane and a back 224 projecting upwardly from the seat so that the seat is disposed forward of the back. The back defines a first patient support surface 226 extending generally in a vertical plane whereas the seat defines a second patient support surface 227 extending generally in a horizontal plane. The seat is mounted in the patient-receiving space of a horizontal field magnet as discussed above. A first antenna 234 extends in or on the back so that it is closely juxtaposed with the first support surface 226. The first antenna has one or more coils with coil vectors $V_{c234}$. A second antenna 235 extends in or on seat 223 so that it is closely juxtaposed with the second support surface 227. The second antenna 235 includes one or more coils with a coil vector $V_{c235}$. Both of these coil vectors are transverse to pole axis 214 and, therefore, both antennas can interact with atomic nuclei in the subject's body. The seat can be supported for pivoting motion and/or for vertical or horizontal movement within the patient-receiving space as discussed above. Even if the seat is pivoted about a horizontal axis parallel to the pole axis, the coil axes of both antennas will remain perpendicular to the pole axis. Apparatus according to this embodiment can be used, for example, to image the spine of a patient in the seated position or to image the perineal region or to image other structures in the patient's body. In particular, the apparatus of FIG. 8 may be advantageously used to image the pelvic region of a patient, as described in commonly assigned U.S. Application No. 60/342,382, filed on Dec. 20, 2001, and commonly assigned non-provisional United States application of Damadian, et al., entitled "MRI Apparatus Including Planar RF Coil Provided in a Seat," filed on even date herewith, the disclosures of which are hereby incorporated by reference herein.

Further in accordance with this aspect of the present invention, the quadrature coil arrangement of FIG. 8 may be achieved in an alternative embodiment by using seat 223 in combination with a planar coil antenna. In particular, first antenna 234 may comprise a planar coil antenna enclosed in a box. The box may then be inserted between support surface 226 and the surface of the patient adjacent to support surface 226, e.g., the patient's back. The second antenna 235 is positioned or arranged so that it is positioned adjacent to the second support surface 227 or the sitting patient. Such a modular arrangement provides for greater flexibility yet while allowing for better signal-to-noise ratio.

The seat and/or the back of a chair as described above with reference to FIG. 8 can be provided as a removable element which can be attached to an elongated, bed-like patient support of the type discussed with reference to FIG. 1. The first and second antennas likewise may be built into these removable elements, or may be provided as separate elements. Methods for attaching and adjusting the seat if implemented as a removable element are disclosed in commonly assigned U.S. application Ser. No. 10/131,843 ("the '843 application"), the disclosure of which is hereby incorporated by reference in its entirety.

Until now the arrangement shown in FIG. 8 was not considered exemplary of a class of antenna or coil arrangements commonly referred to as "quadrature coils." In such an arrangement the coil vectors associated with each of the antennas have mutually perpendicular axes. However, in accordance with this aspect of the present invention, the arrangement of two planar coils as shown in FIG. 8 may be used in a quadrature coil arrangement. In particular, in FIG. 8 the coil vector $V_{C234}$ of antenna 234 is shown as projecting in a generally horizontal direction whereas the coil vector $V_{C235}$ of antenna 235 is shown as projecting in a generally vertical direction. In this way both coil vectors are transverse to each other while being at the same time, as previously noted, transverse to the horizontal magnetic field $B_0$, which is oriented parallel to pole axis 214. As described hereinabove, other novel quadrature coil arrangements are achievable in accordance with this aspect of the present invention. A quadrature coil antenna arrangement advantageously improves the signal-to-noise ratio by a factor up to $\sqrt{2}$. As a practical matter, the quadrature coil arrangement reduces the measurement or MRI scanning time by approximately one-half. That is, a measurement that takes approximately two minutes using a quadrature coil antenna arrangement will take approximately four minutes using another antenna arrangement. This improvement in performance translates into increased efficiency at MRI facilities.

The arrangement shown in FIG. 6 may also be used as a quadrature coil antenna arrangement. In particular, solenoidal or second antenna 150 has a coil vector $V_{C152}$ extending substantially parallel to the axis 153 of the antenna 150. The coil vector $V_{C34'}$ of the first antenna 34' is substantially perpendicular to the coil vector $V_{C152}$ of the of the second antenna 150. The coil vectors of both the first and second antennas, $V_{c34}$, and $V_{C152}$, respectively, are also substantially perpendicular to the static field vector $B_0$. As such, the first and second antennas form a quadrature coil arrangement when used to receive the magnetic resonance signals.

Turning now to FIG. 9, there is illustrated another embodiment of a quadrature coil arrangement. Quadrature coil antenna 300 includes a first antenna schematically depicted as a planar box 302. The one or more coils of the first antenna 302 may be arranged along a planar surface as shown in FIG. 3 and as shown by broken lines 303 in FIG. 9. First antenna 302 defines a coil vector $V_{C302}$ that projects in a direction substantially transverse to the planar surface and, when attached to bed 24, transverse to the patient support surface 26 of the bed 24 (see FIGS. 1 and 2). Quadrature coil antenna 300 includes a second antenna 312 having solenoidal coil portions 314, 316 and 318. The coil vector $V_{C312}$ of the second magnet 312 projects in a direction transverse to the first antenna coil vector $V_{C302}$. Both the first and second coil vectors, $V_{C302}$ and $V_{C312}$, are perpendicular to static field vector $B_0$ of a horizontal field magnet of the type shown in FIGS. 1 and 2. First antenna 302 augments the signal of the second antenna 312 at the depth of the spine, thereby improving the quality of scanned images for this region. The second antenna 312 augments the signal of the first antenna 302 as the distance from the top of the solenoidal coils 314, 316 and 318 increases.

Solenoidal coil portions 314, 316 and 318 and latches 322 and 328 form an integral detachable unit. As depicted, latches 322 and 324 and latches 328 and 330 form male-female pairs that divide the antenna 300 into a front section comprising latches 322 and 328 and solenoidal coil portions 314, 316 and 318 and a bottom section comprising first antenna 302, latch members 324 and 330, locking knobs 340 and 342, and solenoidal coil portions 344, 346 and 348. As such, the quadrature antenna 300 opens in the front by removal of the front section from the back section. Detachable front and bottom sections allow for interchangeable varying size front sections that can optimize the coil size to the patient. In addition, the exposed portion of the solenoidal coil, including the removable front section, comprises a grid-like or skeletonized structure, which results in weight reduction and minimizes claustrophobic patient responses. The front section of quadrature antenna 300 may be optionally left off to allow the first or planar antenna 302 to function as a stand-alone unit.

The quadrature antenna 302 incorporates positioning features that allow the user to attach the coil assembly to the bed 24 of FIGS. 1 and 2 and to vertically adjust the assembly along the bed to accommodate the patient's anatomy. In addition, the positioning features allow an operator to easily lock the coil assembly in place anywhere along the vertical axis of the bed and use the coil with the patient sitting, standing, recumbent or at any angle. Methods and structures for attaching, adjusting and locking an antenna to the bed are disclosed in the '843 application; the same methods and structures can be used to attach, adjust and lock any of the antenna assemblies or arrangements which are described herein.

In a method in accordance with a further aspect of the invention, the quadrature antenna 300 is attached to the patient support 24. A patient P is then disposed on the patient support such that the posterior surface of the patient's torso is closely juxtaposed to the patient support and with first antenna 302. In this way the patient's spine is adjacent to the first antenna 302. The front section of the antenna 300 is then latched into place. As such, the coil vector $V_{C302}$ of the first antenna 302 is perpendicular to the static magnetic field vector $B_0$ and to the support surface 26. The coil vector $V_{C312}$ of the second antenna 312 project in a direction parallel to lengthwise axis 25 while being perpendicular to static magnetic field vector $B_0$. Both antennas are thereby available to receive the magnetic resonance signals emitted from the atomic nuclei of the patient P.

In a further variant, the one or more coils 303 shown in FIG. 9 may be preferably oriented as shown in FIG. 9A. That is, the windings on one or more coils 303' of the planar antenna 302' of FIG. 9A comprise a phased array of two coupled overlapping loops. As shown, the overlap is oriented longitudinally along the patient's body, i.e., along the long axis of the patient's body. In this way, the proximity of the coil to a patient's spinal cord is accomplished, resulting in improved signal-to-noise ratio in the area of interest.

Figure 10:
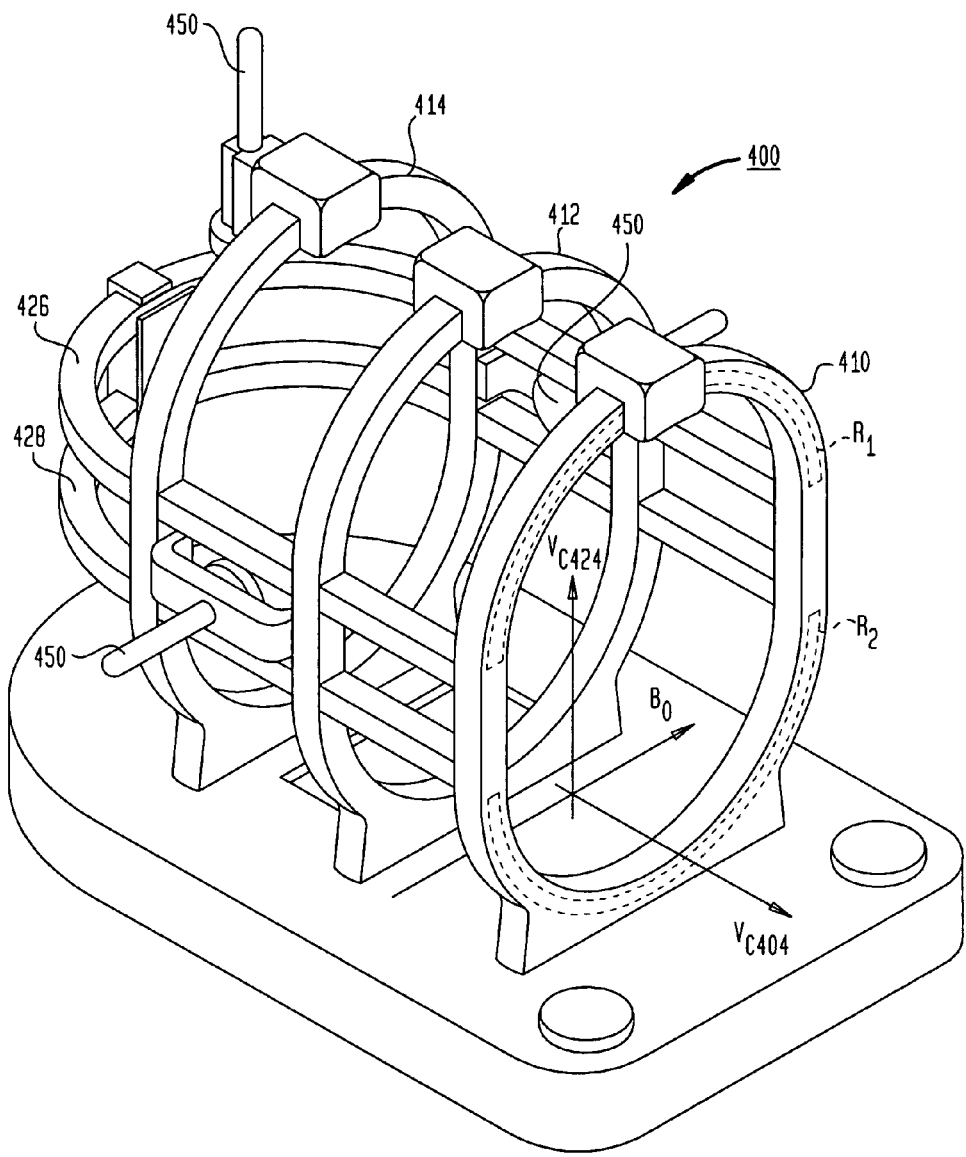
FIG. 10 illustrates another embodiment of a quadrature coil antenna having a solenoidal coil antenna and a saddle coil antenna.

Turning now to FIG. 10, which schematically illustrates another embodiment of a quadrature coil antenna 400 in accordance with the present invention. Quadrature coil antenna 400 comprises receiving solenoidal coil antenna 404 which comprises coils 412 and 414. Solenoidal coil antenna 404 is combined in quadrature mode with a saddle coil 424. One portion of saddle coil antenna 424 comprises the U-shaped coil 426 and an arcuate run $R_1$ transverse to the U-shaped coil 426 along member 430 as shown. Another portion of saddle coil antenna 424 is formed by the U-shaped coil 428 and arcuate run $R_2$, which runs transverse to the U-shaped coil 428 along member 430. As shown, the saddle coil 424 is rotated 90 degrees so that its magnetic sensitivity is now aligned posterior to anterior with respect to a patient's anatomy. The coil vector $V_{C424}$ of the saddle coil antenna 424 projects in a direction perpendicular to static magnetic field vector $B_0$ and to the coil vector $V_{C404}$ of solenoidal coil antenna 404 when used in the apparatus 1 of FIGS. 1 and 2. The coil vector $V_{C404}$ of coil antenna 404 also projects in a direction substantially perpendicular to static magnetic field vector $B_0$.

The solenoidal antenna 404 is mounted onto a base 440. The U-shaped coils of the saddle coil antenna 424 are integrated with the solenoidal antenna 404 to form a skeletal structure into which a patient's head may be inserted. The antenna 400 may be attached to the patient bed 24 via the base 440 and vertically adjusted along the bed to adjust the patient's anatomy. The antenna may also be easily locked into place anywhere along the vertical axis 25 of the bed 24. The attachment, vertical adjustment and locking features are described in the '843 application. The saddle coil 424 enhances the sensitivity in the direction of the static magnetic field vector ($B_0$ in FIGS. 1 and 2). In addition, the patient's line of sight remains unobstructed during a scan which reduces claustrophobic effects. The antenna 400 also includes a convenient and effective left-right and front-back immobilization system comprising adjustable clamps 450, which is adjustable to the patient's anatomy.

In a further variant, the coil 400 may be implemented so as to include separable portions or with a flip-up like visor. In such an embodiment, electrical continuity may be maintained by including male-female sockets at the separation points.

In accordance with an additional method aspect of the present invention, quadrature coil antenna 400 is attached to the patient support 24. A patient P is then disposed on the patient support such that the patient's head is placed in the quadrature coil antenna 400. Stabilizing clamps 450 may then be used to stabilize the patient's head. In this position, the coil vector $V_{C404}$ of solenoidal coil antenna 404 projects in a direction parallel to lengthwise axis 25 and perpendicular to static field vector $B_0$. Saddle coil vector $V_{C424}$ projects in a direction transverse to the support surface 26 and is also perpendicular to static field vector $B_0$. The patient's head may then be scanned with the patient support rotated or positioned in the many orientations discussed hereinabove. In particular, the adjustable clamps 450 provide stabilization with the patient rotated or tilted in many positions previously discussed hereinabove in relation to FIGS. 1, 2 and 5.

Figure 11A:
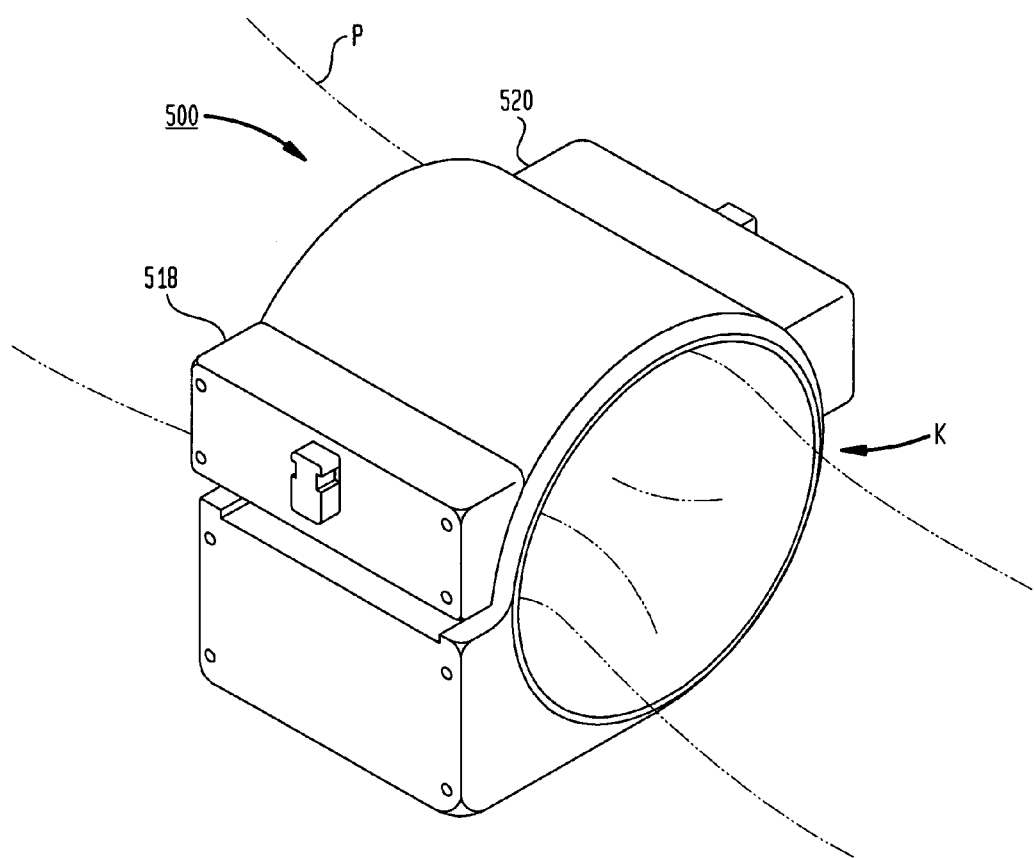
FIG. 11A illustrates a schematic of yet another embodiment of a quadrature coil antenna having a solenoidal coil antenna and a saddle coil antenna.
Figure 11B:
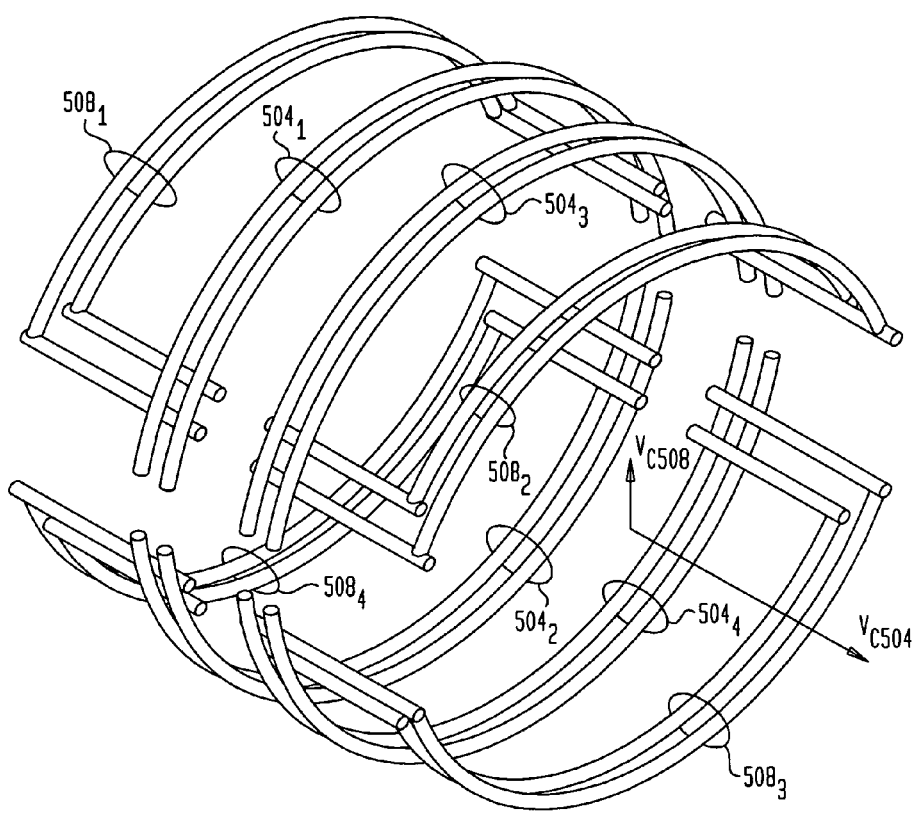
FIG. 11B illustrates the quadrature coil antenna of FIG. 11A without the external casing so as to reveal the arrangement of the solenoidal and saddle coil antennas.

Turning now to FIG. 11A, there is illustrated a schematic of yet another quadrature coil antenna in accordance with an aspect of the present invention. Quadrature coil 500 is used for preferably imaging a patient's knee. As can be best seen from FIG. 11B, quadrature coil 500 comprises a solenoidal-receiver coil 504 and a saddle-style receiver coil 508. Solenoidal-coil receiver 504 comprises individual coils $504_1$, $504_2$, $504_3$ and $504_4$. In particular, coils $504_4$ and $504_3$ form one solenoidal loop and coils $504_1$ and $504_2$ form another solenoidal loop. This solenoidal coil vector $V_{C504}$ projects in a direction perpendicular to static field vector $B_0$ when used in the apparatus 1 of FIGS. 1 and 2. Saddle coil 508 comprises coil members $508_1$, $508_2$, $508_3$ and $508_4$. Coil members $508_1$ and $508_2$ form a continuous loop comprising the upper portion of saddle coil 508. Saddle coil members $508_3$ and $508_4$ form another loop comprising the lower portion of saddle coil receiver 508. A saddle-coil vector $V_{c508}$ projects in a direction perpendicular to static-magnetic field $V_0$ when used in the apparatus 1 of FIGS. 1 and 2. As FIG. 11B shows, the windings of the solenoidal coils 504 encircle the windings of the saddle coils 508.

In a first embodiment, knee-coil 500 may be implemented to open at latch members 518 and 520 (see FIG. 11A.) A patient's knee K is then positioned within knee-coil 500 and the antenna assembly is completed by latching members 518 and 520. In accordance with this first embodiment of knee coil 500, electrical continuity can be maintained by including male-female members where solenoidal coils $504_1$ through $504_4$ need to be mated. The patient is then placed on support surface 26. Support surface 26 or table 24 is then moved into position so that the patient's knee is within the static-magnetic field. Imaging then proceeds. In accordance with the present invention, such imaging may proceed under a weight bearing or non-weight bearing condition.

In accordance with a further variant, knee coil 500 may be implemented as a single integrated unit, which is then pulled over a patient's foot up to the patient's knee. In addition, the knee coil 500 may also be implemented such that it swings open at either latch 518 or 520.

Figure 12:
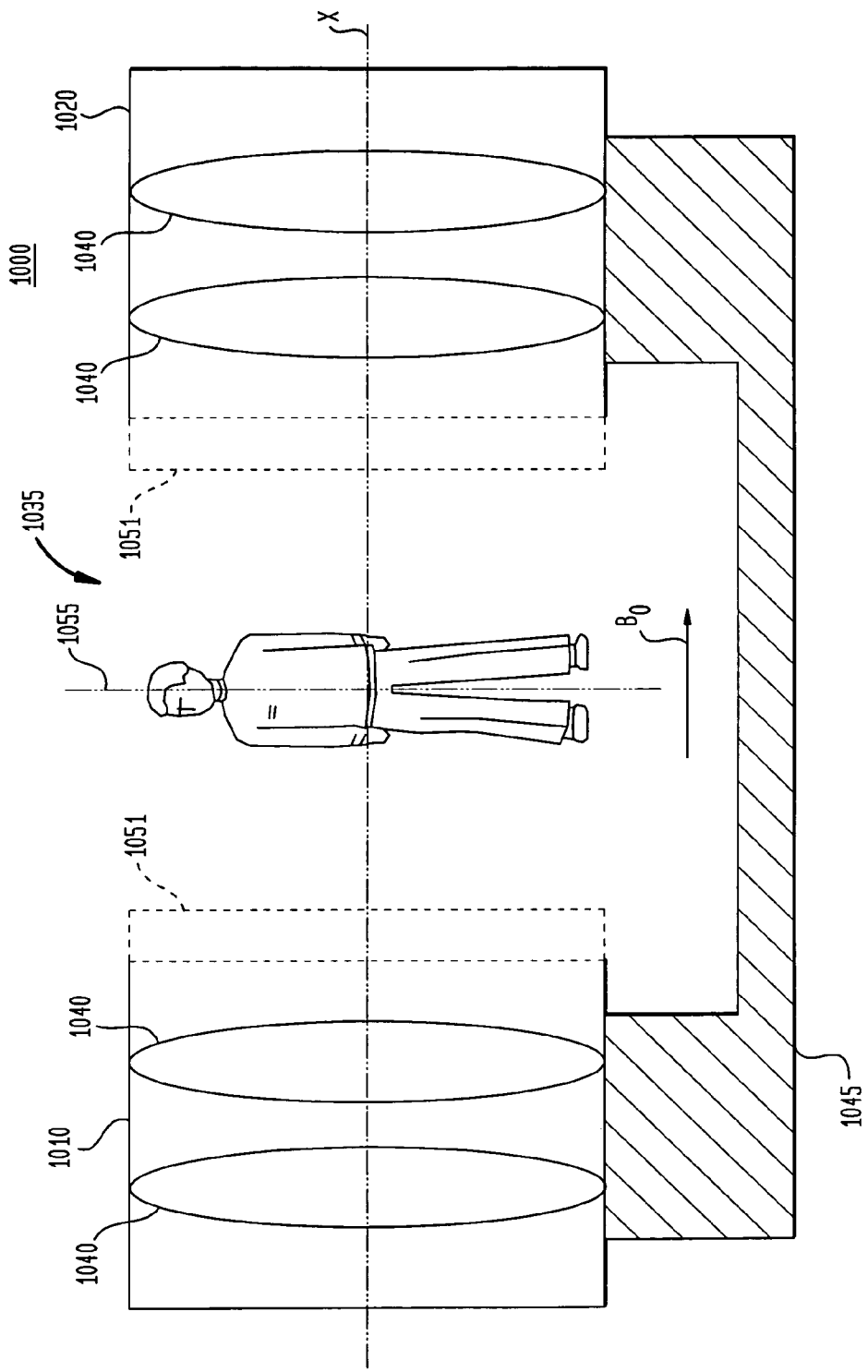
FIG. 12 schematically illustrates another embodiment of resonance imaging magnet in accordance with the present invention.

In addition to the magnet structure shown in FIGS. 1, 2 and 5, the quadrature coil arrangement described hereinabove may also be used in a magnet structure 1000, as shown in FIG. 12. The magnet 1000 includes a stationary magnet having a pair of elements, 1010 and 1020, spaced apart from one another along horizontal axis X. A magnetic air gap between elements 1010 and 1020 define a patient-receiving space 1035. Each of the elements 1010 and 1020 include one or more solenoidal superconducting coils 1040. The coils 1040 are operative to direct magnetic flux between the elements 1010 and 1020 so as to establish a horizontal static magnetic field $B_0$. The elements 1010 and 1020 are mounted to structural support member 1045, which maintains the gap between the elements. The magnet 1000 may optionally include ferromagnetic poles 1051. However, poles 1051 may be eliminated and the magnet 1000 may nonetheless operate in accordance with the present invention.

In accordance with the embodiment shown in FIG. 12, a patient P may be positioned within the patient-receiving space 1035 such that the long axis 1055 of the patient's body is transverse to static magnetic $B_0$. The patient may be positioned in the sitting or standing position in accordance with the requirements associated with the medical procedure. In addition, the patient may also be fitted with any of the quadrature coil antennas described in detail hereinabove so that magnetic resonance scanning may be advantageously performed. In particular, the signal-to-noise ratios improvement of up to $\sqrt{2}$ may be achieved in accordance with this embodiment.

Figure 13:
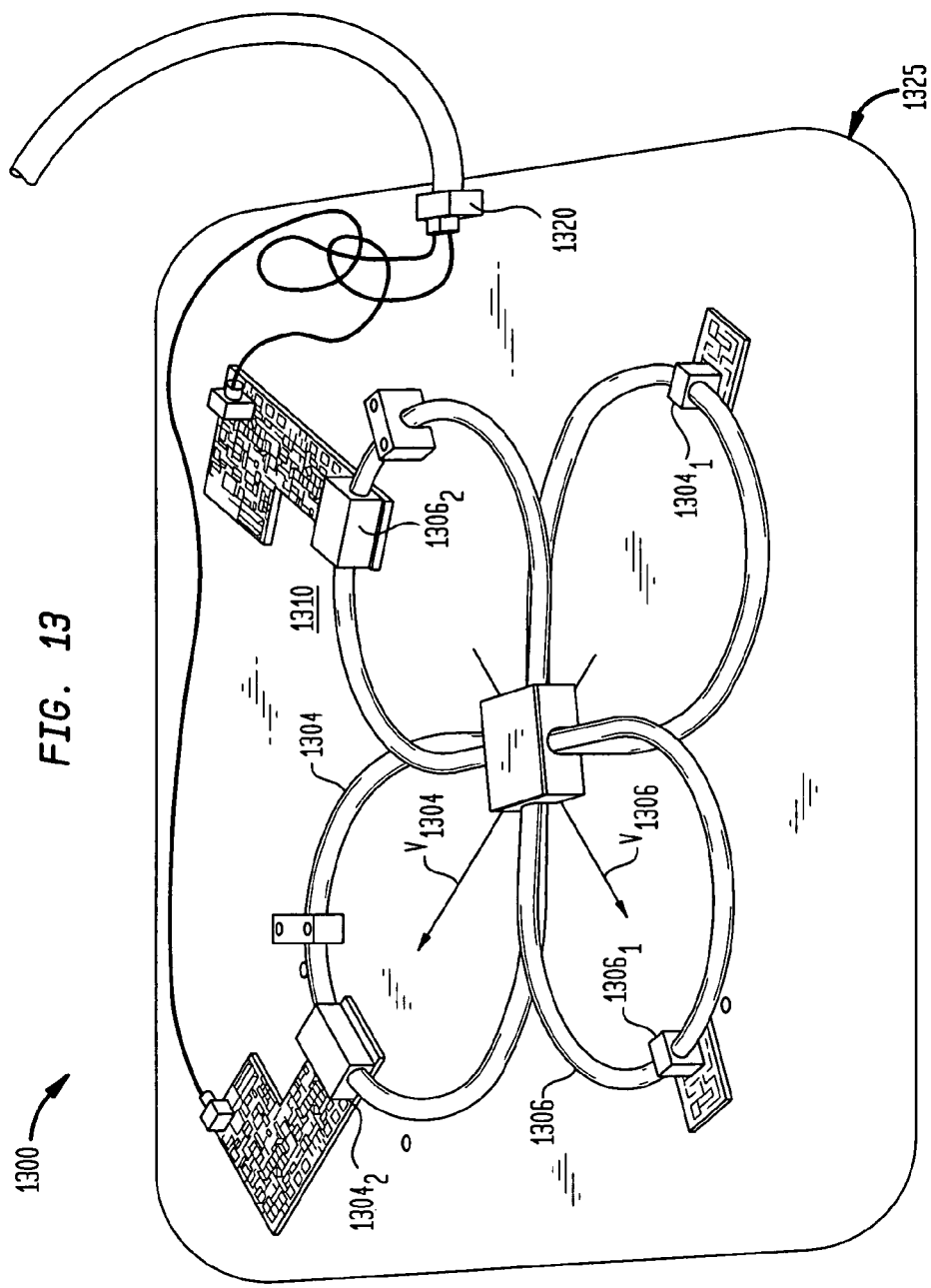
FIG. 13 schematically illustrates an antenna assembly in accordance with an aspect of the present invention.

Turning now to FIG. 13, there is shown a quadrature surface coil antenna 1300 in accordance with a further aspect of the present invention. The antenna 1300 includes a pair of substantially flat butterfly receiver coils 1304, 1306 that are arranged in quadrature mode as shown. In particular, a first coil vector $V_{1304}$ of coil 1304 is oriented parallel to a plane in which the receiver coil 1304 lies. A second coil vector $V_{1306}$ of coil 1306 is also oriented perpendicular to first coil vector $V_{1304}$ and parallel to a plane in which receiver coil 1306 lies. In the preferred embodiment, the coils 1304, 1306 are mounted to a base 1310 that forms a planar structure or box for housing the quadrature surface coil antenna 1300. The planar structure or box is shown without a top that is attachable to the base 1310 so as to conveniently reveal the arrangement of the butterfly coils 1304, 1306. In accordance with this aspect of the present invention, the coils vectors are oriented parallel to surface of the planar structure or box.

As shown, each coil 1304, 1306 includes a pair of tap off points $1314_{1,2}$, $1316_{1,2}$ at which circuitry necessary to the operation of the coils may be located. Such circuitry serve to decouple the individual antennas, define a resonant antenna circuit and output the magnetic resonance signals received (e.g., see output port 1320).

The quadrature surface coil antenna 1300 may be used in the apparatus 1 shown in FIG. 2 by positioning the structure housing the antenna 1300 parallel to surface of the poles 12. In particular, a side of the structure or planar box 1310 is positioned adjacent to the patient supporting surface 26 such that each of the coil vectors $V_{1304}$, $V_{1306}$ are substantially orthogonal or perpendicular to the horizontal pole axis 14 and the direction of the static magnetic field $B_0$. Since the geometry of the butterfly coils allow for 360° of freedom in positioning the structure or box 1310 in any plane parallel with the pole surfaces, the antenna assembly 1300 can be rotated into any orientation in such a plane to complement the patient anatomy. The magnetic sensitivity of the coils can be rotated from posterior/anterior to inferior/superior and any point in between that suits the anatomical surfaces. The antenna 1300 may be useful in imaging the spine or other portions of a patient's anatomy.

In addition, the quadrature coil antenna 1300 is advantageously circularly polarized in a plane perpendicular to the direction of the static magnetic field $B_0$. The antenna 1300 desirably produces it strongest magnetic sensitivity at the intersection of the butterfly elements. Therefore, the symmetry of the arrangement produces an even circular illumination of the anatomy with signal-to-noise that is approximately 40% greater than a single butterfly coil. As discussed, the antenna 1300 is preferably flat and is positionable parallel to the surface of the poles of the magnet. However, the antenna may be similarly used even in a magnet without distinct poles as long as the coil vectors are oriented perpendicular to the direction of the static magnetic field. As such, the quadrature surface 1300 is also adaptable to imaging in a vertical field system with the coil surface parallel to the patient support surface.

Figure 14:
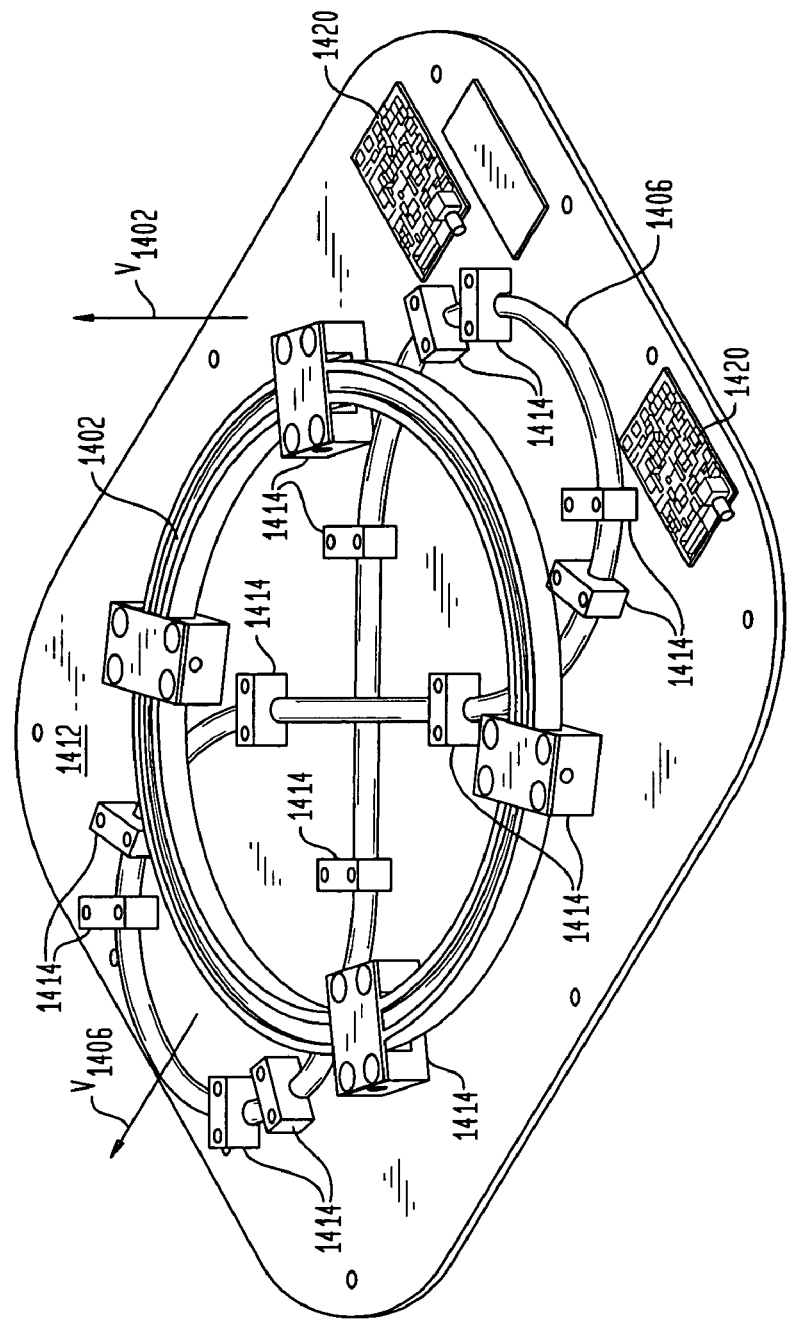
FIG. 14 schematically illustrates an antenna assembly in accordance with an aspect of the present invention.

Turning now to FIG. 14, there is shown a quadrature planar coil antenna assembly 1400 in accordance with an additional aspect of the present invention. As shown, the assembly 1400 includes a loop coil antenna 1402 and a butterfly coil antenna 1406 mounted to a base or support 1412 using a plurality of mounting members 1414. As shown, each mounting member conveniently includes an opening large enough to accommodate a portion of the coil and secures the coil to base 1412 via various mounting screws. The loop coil antenna 1402 includes a coil vector $V_{1402}$ perpendicular to the surface of the base 1412. The butterfly coil 1406 includes a coil vector $V_{1406}$ that is parallel to the surface of the base 1412. The assembly also includes circuitry 1420 (shown not connected) for outputting magnetic resonance signals received by the coils. Such circuitry serves to decouple the individual antennas, define a resonant antenna circuit and output the magnetic resonance signals received by the antenna coils.

In accordance with this aspect of the present invention, the planar coil assembly 1400 may be used with the system of FIGS. 1 and 2 with a patient oriented in any position between an upright and recumbent position as long as the coil vectors $V_{1402}$, $V_{1406}$ are perpendicular to the static magnetic filed $B_0$. In particular, while the loop coil's magnetic sensitivity is aligned posterior to anterior with respect to the patient's anatomy, the butterfly coil's magnetic sensitivity is aligned inferior to superior or vice versa. In accordance with an aspect of the present invention, a patient may be positioned in an upright position, as shown in FIG. 2 for example, with the antenna assembly 1400 between a surface of the patient's anatomy and the surface of the patient support device 24. Although FIGS. 1 and 2 depict the antenna as being adjacent to the posterior surface of the patient P, the antenna may be positioned adjacent to the anterior surface of the patient. The antenna 1400 may be vertically adjusted along the support surface 26 to allow for imaging of the spine, heart, or other areas of the torso. In addition, the antenna may be positioned as shown in FIG. 8 so as to allow a patient to sit on the antenna so that images of the lower abdomen, e.g., pelvic region or prostate, can be obtained.

In accordance with this aspect of the present invention, the loop coil typically augments the signal of the butterfly coil where the butterfly coil tends to be weakest. In addition, the butterfly coil typically augments the signal received by the loop coil where the loop coil tends to be weakest. The antenna coil 1400 is advantageously circularly polarized in a plane perpendicular to the horizontal field $B_0$ of the magnet. Therefore, the antenna coil 1400 may used in any magnet geometry where the antenna coil is circularly polarized in a plane perpendicular to the horizontal field of the magnet.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. In particular, quadrature coils may be designed for many more parts of the human anatomy, e.g., the ankle, wrist, shoulder, neck, foot, breast, etc., that would provide improved signal-to-noise ratio performance.

The invention claimed is:

1. Apparatus for magnetic resonance imaging, comprising:
a magnet defining a patient-receiving space and having a static magnetic field with a field vector in a substantially horizontal direction;
a patient support having a support surface for a human body, said patient support being positioned within said patient-receiving space and being pivotable about a horizontal pivot axis; and
a quadrature coil antenna arrangement for receiving a signal from a patient disposed within said receiving space, said quadrature coil antenna including a first antenna having a first coil vector and a second antenna having a second coil vector, said first coil vector and said second coil vector being transverse to said static magnetic field vector, and wherein said static magnetic field vector is oriented substantially transverse to the long axis of a patient disposed within said patient-receiving space,
wherein said first antenna and said second antenna comprise coil antennas configured in a dual butterfly geometry housed in a planar structure and wherein the position of the planar structure can be adjusted along a lengthwise direction of the patient support surface perpendicular to said magnetic field axis.

2. The apparatus as claimed in claim 1, wherein said first and second coil vectors are transverse to each other.

3. The apparatus as claimed in claim 2, wherein said planar structure is oriented such that its surface lies in a plane perpendicular to said magnetic field axis.

4. The apparatus as claimed in claim 2, wherein said planar structure comprises a quadrature surface coil that is circularly polarized in a plane perpendicular to said magnetic field axis.

5. The apparatus as claimed in claim 1, further comprising an elevator for raising and lowering said patient support relative to said magnet while the patient support is holding the patient in an upright orientation so as to position any part of the patient within said patient-receiving space.

6. The apparatus as claimed in claim 1, wherein said first antenna and said second antenna are substantially flat.

7. The apparatus as claimed in claim 1, wherein said first coil vector is oriented parallel to a plane in which said first antenna lies and said second coil vector is oriented perpendicular to said first coil vector and parallel to a plan in which said second antenna lies.

8. The apparatus as claimed in claim 1, wherein said first coil vector and said second coil vector are oriented parallel to said planar structure.

* * * * *

UNITED STATES PATENT AND TRADEMARK OFFICE
CERTIFICATE OF CORRECTION

| | | |
|---|---|---|
| PATENT NO. | : 7,701,209 B1 | Page 1 of 1 |
| APPLICATION NO. | : 10/998395 | |
| DATED | : April 20, 2010 | |
| INVENTOR(S) | : Charles A. Green | |

It is certified that error appears in the above-identified patent and that said Letters Patent is hereby corrected as shown below:

Column 2, line 68, "patient can" should read --patient, can--.
Column 3, line 41, "second coil vector" should read --second coil vectors--.
Column 3, line 53, "antennas being" should read --antennas are--.
Column 4, line 14, "method for" should read --a method for--.
Column 4, line 65, "about an" should read --about a--.
Column 5, line 39, "as loop" should read --as a loop--.
Column 6, line 23, "having solenoidal" should read --having a solenoidal--.
Column 6, line 26, "having solenoidal" should read --having a solenoidal--.
Column 6, line 37, "embodiment of" should read --embodiment of a--.
Column 7, line 56, "thin, plate" should read --thin plate--.
Column 11, line 9, "of the of the second" should read --of the second--.
Column 12, line 9, "312 project" should read --312 projects--.
Column 12, line 21, "resulting in" should read --resulting in an--.
Column 13, line 60, "1020 include" should read --1020 includes--.
Column 14, line 30, "the coils" should read --the coils'--.
Column 14, line 43, "are substantially" should read --is substantially--.
Column 14, line 46, "coils allow" should read --coils allows--.
Column 14, line 58, "produces it" should read --produces its--.
Column 15, line 51, "may used" should read --may be used--.
Column 16, line 51, "a plan in" should read --a plane in--.

Signed and Sealed this
Fourteenth Day of June, 2011

David J. Kappos
*Director of the United States Patent and Trademark Office*